US012760009B2

(12) United States Patent
Polla et al.

(10) Patent No.: US 12,760,009 B2
(45) Date of Patent: Oct. 13, 2026

(54) CERTAIN 3-AZABICYCLO[3.1.0]HEXANES AS GLP-1 RECEPTOR MODULATORS

(71) Applicant: AstraZeneca AB, Sodertalje (SE)

(72) Inventors: Magnus Polla, Sodertalje (SE); Joakim Bergman, Sodertalje (SE); Johan Sundell, Sodertalje (SE); Jonas Brånalt, Sodertalje (SE); Johan Kajanus, Sodertalje (SE); Ekaterina Ratkova, Sodertalje (SE); Magnus Johansson, Sodertalje (SE)

(73) Assignee: ASTRAZENECA AB, Sodertalje (SE)

( * ) Notice: Subject to any disclaimer, the term of this patent is extended or adjusted under 35 U.S.C. 154(b) by 283 days.

(21) Appl. No.: 18/718,837

(22) PCT Filed: Dec. 15, 2022

(86) PCT No.: PCT/EP2022/086080
§ 371 (c)(1),
(2) Date: Jun. 12, 2024

(87) PCT Pub. No.: WO2023/111145
PCT Pub. Date: Jun. 22, 2023

(65) Prior Publication Data

US 2025/0042882 A1 Feb. 6, 2025

Related U.S. Application Data

(60) Provisional application No. 63/265,493, filed on Dec. 16, 2021.

(51) Int. Cl.
*C07D 405/14* (2006.01)
*A61K 31/4184* (2006.01)
*A61K 31/4439* (2006.01)

(52) U.S. Cl.
CPC ........ *C07D 405/14* (2013.01); *A61K 31/4184* (2013.01); *A61K 31/4439* (2013.01)

(58) Field of Classification Search
CPC .................................................... C07D 405/14
See application file for complete search history.

(56) References Cited

FOREIGN PATENT DOCUMENTS

| | | | |
|---|---|---|---|
| CN | 113480534 | A | 10/2021 |
| CN | 113493447 | A | 10/2021 |
| CN | 113816948 | A | 12/2021 |
| CN | 113831337 | A | 12/2021 |
| CN | 114478497 | A | 5/2022 |
| CN | 114591296 | A | 6/2022 |
| CN | 114591308 | A | 6/2022 |
| CN | 114634510 | A | 6/2022 |
| CN | 114716423 | A | 7/2022 |
| CN | 114763352 | A | 7/2022 |
| CN | 114805336 | A | 7/2022 |
| CN | 114907351 | A | 8/2022 |
| WO | 2018109607 | A1 | 6/2018 |
| WO | 2019239319 | A1 | 12/2019 |
| WO | 2019239371 | A1 | 12/2019 |
| WO | 2020103815 | A1 | 5/2020 |
| WO | 2020207474 | A1 | 10/2020 |
| WO | 2020234726 | A1 | 11/2020 |
| WO | 2020263695 | A1 | 12/2020 |
| WO | 2021018023 | A1 | 2/2021 |
| WO | 2021081207 | A1 | 4/2021 |
| WO | 2021096284 | A1 | 5/2021 |
| WO | 2021096304 | A1 | 5/2021 |
| WO | 2021112538 | A1 | 6/2021 |
| WO | 2021116874 | A1 | 6/2021 |
| WO | 2021154796 | A1 | 8/2021 |
| WO | 2021160127 | A1 | 8/2021 |
| WO | 2021197464 | A1 | 10/2021 |
| WO | 2021219019 | A1 | 11/2021 |
| WO | 2021244645 | A1 | 12/2021 |
| WO | 2021249492 | A1 | 12/2021 |
| WO | 2021254470 | A1 | 12/2021 |

(Continued)

OTHER PUBLICATIONS

Bailey C.J., "GIP Analogues and the Treatment of Obesity-diabetes", Peptides, vol. 125, Article 170202, Mar. 2020, pp. 1-26.
Berge S.M., et al., "Pharmaceutical Salts," Journal of Pharmaceutical Sciences, vol. 66, No. 1, Jan. 1977, pp. 1-19, XP002675560.
Buse J.B., et al., "2019 Update to: Management of Hyperglycemia in Type 2 Diabetes, 2018. A Consensus Report by the American Diabetes Association (ADA) and the European Association for the Study of Diabetes (EASD)", Diabetes Care, vol. 43, No. 2, Feb. 2020, pp. 487-493.
Davies M., et al., "Effect of Oral Semaglutide Compared With Placebo and Subcutaneous Semaglutide on Glycemic Control in Patients With Type 2 Diabetes: A Randomized Clinical Trial", JAMA, vol. 318, No. 15, Oct. 17, 2017, pp. 1460-1470.
Eckel R.H., et al., "The Metabolic Syndrome", Lancet, vol. 365, No. 9468, Apr. 2005, pp. 1415-1428.

(Continued)

*Primary Examiner* — Andrew D Kosar
*Assistant Examiner* — Connor K English
(74) *Attorney, Agent, or Firm* — Global IP ASTRAZENECA

(57) ABSTRACT

There are disclosed certain 3-azabicyclo[3.1.0]hexanes, and pharmaceutically acceptable salts thereof, together with compositions containing them and their use in therapy. The compounds are GLP-1 receptor modulators and are thereby particularly useful in the treatment or prophylaxis of cardiovascular disease and metabolic conditions, for example Type 2 diabetes.

(I)

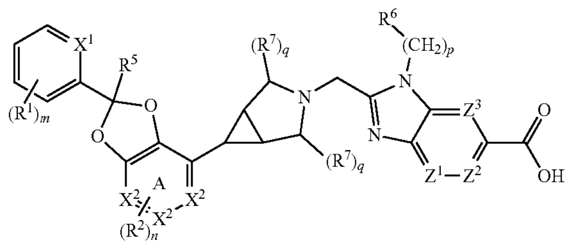

7 Claims, No Drawings

(56) References Cited

FOREIGN PATENT DOCUMENTS

| | | | |
|---|---|---|---|
| WO | 2022007979 | A1 | 1/2022 |
| WO | 2022028572 | A1 | 2/2022 |
| WO | 2022031994 | A1 | 2/2022 |
| WO | 2022040600 | A1 | 2/2022 |
| WO | 2022042691 | A1 | 3/2022 |
| WO | 2022068772 | A1 | 4/2022 |
| WO | 2022078152 | A1 | 4/2022 |
| WO | 2022078380 | A1 | 4/2022 |
| WO | 2022078407 | A1 | 4/2022 |
| WO | 2022109182 | A1 | 5/2022 |
| WO | 2022111624 | A1 | 6/2022 |
| WO | 2022165076 | A1 | 8/2022 |
| WO | 2022184849 | A1 | 9/2022 |
| WO | 2022192428 | A1 | 9/2022 |
| WO | 2022192430 | A1 | 9/2022 |
| WO | 2022199458 | A1 | 9/2022 |
| WO | 2022199661 | A1 | 9/2022 |
| WO | 2022202864 | A1 | 9/2022 |
| WO | 2022216094 | A1 | 10/2022 |
| WO | 2022219495 | A1 | 10/2022 |
| WO | 2022225914 | A1 | 10/2022 |
| WO | 2022225941 | A1 | 10/2022 |
| WO | 2022228490 | A1 | 11/2022 |
| WO | 2022235717 | A1 | 11/2022 |

OTHER PUBLICATIONS

Griffith D.A., et al., "A Small-Molecule Oral Agonist of the Human Glucagon-like Peptide-1 Receptor", Journal of Medicinal Chemistry, vol. 65, No. 12, Jun. 23, 2022, pp. 8208-8226.

Holst J.J., "From the Incretin Concept and the Discovery of GLP-1 to Today's Diabetes Therapy", Frontiers in Endocrinology, vol. 10, Article 260, Apr. 2019, pp. 1-10.

International Search Report and Written Opinion for International Application No. PCT/EP2022/086080, dated Mar. 15, 2023, 10 pages.

Kahn S.E., et al., "Pathophysiology and Treatment of Type 2 Diabetes: Perspectives on the Past, Present, and Future", Lancet, vol. 383, No. 9922, Mar. 22, 2014, pp. 1068-1083.

Ma H., et al., "Structural Insights into the Activation of GLP-1R by a Small Molecule Agonist", Cell Research, vol. 30, No. 12, Dec. 2020, pp. 1140-1142.

Miller C.L., et al., "Targeting Cyclic Nucleotide Phosphodiesterase in the Heart: Therapeutic Implications", Journal of Cardiovascular Translational Research, vol. 3, No. 5, Jul. 15, 2010, pp. 507-515.

Movsesian M.A., et al., "Phosphodiesterase Inhibition in Heart Failure", In: Phosphodiesterases as Drug Targets, Handbook of Experimental Pharmacology, vol. 204, 2011, pp. 237-249.

Nauck M.A., et al., "Secretion of Incretin Hormones (GIP and GLP-1) and Incretin Effect After Oral Glucose in First-degree Relatives of Patients with Type 2 Diabetes", Regulatory Peptides, vol. 122, No. 3, Nov. 15, 2004, pp. 209-217.

Nauck M.A., et al., "Incretin Hormones: Their Role in Health and Disease", Diabetes, Obesity and Metabolism, vol. 20, Suppl. 1, Feb. 2018, pp. 5-21.

Nauck M.A., et al., "Normalization of Fasting Hyperglycaemia by Exogenous Glucagon-like Peptide 1 (7-36 Amide) in Type 2 (Non-insulin-dependent) Diabetic Patients", Diabetologia, vol. 36, No. 8, Aug. 1993, pp. 741-744.

Rautio J., et al., "Prodrugs: Design and Clinical Applications", Nature Reviews Drug Discovery, vol. 7, Mar. 2008, pp. 255-270.

Tsonkova V.G., et al., "The EndoC-bH1 Cell Line Is a Valid Model of Human Beta Cells and Applicable for Screenings to Identify Novel Drug Target Candidates", Molecular Metabolism, vol. 8, Feb. 2018, pp. 144-157.

CERTAIN 3-AZABICYCLO[3.1.0]HEXANES AS GLP-1 RECEPTOR MODULATORS

TECHNICAL FIELD

The technical field relates to certain 3-azabicyclo[3.1.0] hexanes, to their use in the treatment of cardiovascular disease and metabolic conditions, for example type 2 diabetes, and to pharmaceutical compositions containing them.

BACKGROUND

Obesity and type 2 diabetes (T2D) are major and growing health problems worldwide (*Lancet,* 2014, 9922, 1068-1083). The two diseases are strongly associated with each other, with obesity proceeding development of insulin resistance and T2D. T2D is associated with several comorbidities including cardiovascular disease, renal disease, hypertension, stroke, non-alcoholic fatty liver disease (NAFLD) and non-alcoholic steatohepatitis (NASH) (*Lancet,* 2005, 9468, 1415-1428).

Incretin hormones including GLP-1 (glucagon-like peptide-1) and GIP (glucose-dependent insulinotropic polypeptide) are gut peptides that are secreted after nutrient intake and stimulate insulin secretion (*Diabetes Obes Metab.,* 2018, 20(Suppl. 1), 5-21). GLP-1 secretion from the gut is impaired in obese subjects which may indicate a role in the pathophysiology of obesity (*Regulatory Peptides,* 2004, 122, 209-217).

GLP-1 is secreted from the L-cells in the lower gut in response to food intake. GLP-1 stimulates insulin secretion from the pancreatic P-cells, in a glucose dependent manner (*Diabetologia,* 1993, 36, 741-744). GLP-1 also inhibits glucagon secretion, reduces appetite and slows down gastric emptying. The GLP-1 receptor is also present in the heart, kidneys and immune system and activation has been shown to reduce blood pressure, increase natriuresis and decrease inflammation.

GLP-1 is a 37-amino acid peptide, post-translationally processed from pro-glucagon, a 158 amino acid precursor polypeptide (www.uniprot.org, pro-glucagon entry P01275). Several other peptides are also derived from proglucagon and processed in a tissue specific manor, including glucagon and oxyntomodulin. GLP-1 has very short half-life in vivo as it is rapidly degraded by dipeptidyl peptidase-4 (DPP-IV) (*Front. Endocrinol.* 2019, 10, Article 260, 1-10).

Incretin-based glucose- and body weight-lowering medications include GLP-1 receptor agonists, DPP-IV inhibitors and more recently also combinations of GLP-1 agonists and glucose-dependent insulinotropic polypeptide (GIP) agonists (Peptides, 2020, 125, Article 170202). Traditionally GLP-1 analogues are peptide hormones which have been modified to minimize DPP-IV cleavage and are administered as injectables. The first oral GLP-1 peptide was recently approved but bioavailability is low and the drug needs to be administered in the fasting state, 30 min before nutrient intake which may limit patient compliance (*JAMA,* 2017, 318(15), 1460-1470). The injectable peptides show increased efficacy over the oral peptides but are limited by the route of administration. Small molecule GLP-1 receptor agonists are in development from several companies and are expected to provide a therapeutic benefit versus peptide based therapies due to early use in the treatment paradigm.

Pharmacological stimulation of GLP-1 receptors has been shown to significantly reduce HbA1c levels, provide long term weight loss and reduce blood pressure. GLP-1 receptor agonists have also been shown to reduce cardiovascular events and prolong life in high-risk patients with T2D and are therefore recommended by the European Association for the Study of Diabetes (EASD) and American Diabetes Association (ADA) in patients with multiple risk factors of cardiovascular disease (CVD) independent of the patients glycemic control (Diabetes Care, 2020, 43, 487-493).

There remains a need for an easily-administered prevention and/or treatment for cardiometabolic and associated diseases.

WO2018/109607 discloses 6-carboxylic acids of benzimidazoles and 4-aza-, 5-aza-, 7-aza- and 4,7-diazabenzimidazoles as GLP-1 receptor agonists, processes to make said compounds, and methods comprising administering said compounds to a mammal in need thereof.

WO2019/239319 and WO2019/239371 disclose 6-carboxylic acids of benzimidazoles and 4-aza-, 5-aza- and 7-aza-benzimidazoles as GLP-1 receptor agonists, processes to make said compounds, and methods comprising administering said compounds to a mammal in need thereof.

WO2020/103815 disclose GLP-1 receptor agonist compounds and pharmaceutical compositions thereof, for use in e.g. treating type 2 diabetes mellitus, pre-diabetes, obesity, non-alcoholic fatty liver disease, non-alcoholic steatohepatitis and cardiovascular disease.

WO2020/207474 disclose GLP-1 receptor agonist compounds and pharmaceutical compositions thereof, for use in e.g. treating type 2 diabetes mellitus, pre-diabetes, obesity, non-alcoholic fatty liver disease, non-alcoholic steatohepatitis and cardiovascular disease.

WO2020/234726 disclose combinations of GLP-1 receptor agonist compounds and pharmaceutical compositions thereof and an acetyl-CoA carboxylase (ACC) inhibitor or a diacylglycerol acyltransferase (DGAT2) inhibitor, or a ketohexokinase (KHK) inhibitor or farnesoid X receptor (FXR) agonist, for use in e.g. treating type 2 diabetes mellitus, pre-diabetes, obesity, non-alcoholic fatty liver disease, non-alcoholic steatohepatitis and related diseases.

WO2020/263695 discloses glucagon-like peptide-1 receptor agonists and therapeutic uses of the compounds to treat type II diabetes mellitus.

WO2021/081207 discloses compounds that bind to and act as agonists or modulators of the glucagon-like peptide-1 receptor (GLP-1R) and act as agonists or modulators of GLP-1R. The disclosure further relates to the use of the compounds for the treatment and/or prevention of diseases and/or conditions by said compounds.

WO2021/018023 discloses compounds for modulating a Glucagon-like peptide-1 (GLP-1) receptor, and a pharmaceutical use thereof.

WO2021/096284 and WO2021/096304 discloses compounds that act as GLP-1 receptor agonists, for use as therapeutic agents for metabolic diseases.

WO2021/112538 discloses compounds which serves as a GLP-1 receptor agonist and may be useful in the prevention or treatment of a disease associated with GLP-1 activity.

WO2021/154796 discloses GLP-1R agonists, and compositions, methods, and kits thereof. Such compounds are generally useful for treating a GLP-1R mediated disease or condition.

WO2021/160127 discloses GLP-1 agonists, pharmaceutical compositions, and methods of use thereof.

WO2021116874 discloses of solid forms of 2-[[4-[(S)-2-(5-chloropyridin-2-yl)-2-methylbenzo[d][1,3]dioxol-4-yl] piperidin-1-yl]methyl]-1-[[(S)-oxetan-2-yl]methyl]-1H-benzo[d]imidazole-6-carboxylic acid, 1,3-dihydroxy-2-(hydroxymethyl)propan-2-amine salt for pharmaceutical use.

CN113493447A discloses a compound that can be used as a GLP-1 receptor agonist. WO2021197464 discloses fused imidazole derivatives, preparation methods and medical use as a therapeutic agent, especially as GLP-1 receptor agonists.

CN113480534A discloses benzimidazole or azabenzimidazole-6-carboxylate compound that can activate GLP-1R downstream signaling pathway.

WO2021154796 discloses compounds as GLP-1R agonists, and compositions, methods, and kits thereof.

WO2021219019 discloses GLP-1 agonists of formula I, including pharmaceutically acceptable salts and solvates thereof, pharmaceutical compositions, and methods of using the same.

WO2021244645 discloses five-membered heteroaromatic imidazole compounds I and their medical use.

WO2021249492 discloses methyl-substituted benzobisoxazole compound and the use thereof in the preparation of drugs for treating related diseases.

CN113816948A discloses fused imidazole derivatives as GLP-1 receptor agonist in the treatment of diabetes.

WO2021254470 discloses preparation of 6-oxo-3,6-dihydropyridine derivative and a pharmaceutical composition containing the derivative, are used as therapeutic agents, in particular as GLP-1 receptors agonist and in the preparation of drugs for the treatment and/or prevention of diabetes.

WO2022007979 discloses a fused imidazole derivative, a preparation method therefor, a pharmaceutical composition containing the derivative, and the use of same as a therapeutic agent, in particular the use thereof as a GLP-1 receptor agonist.

CN113831337A discloses heterocyclic nitrogen compounds as GLP-1 receptor agonist.

WO2022068772 discloses a kind of benzimidazole derivative, its preparation method and application as GLP-1R agonists.

WO2022042691 discloses GLP-1 agonists, including pharmaceutically acceptable salts and solvates thereof, and pharmaceutical compositions including the same.

WO2022040600 discloses compounds that may be used as a glucagon-like peptide-1 receptors (GLP-1R) agonist.

WO2022028572 discloses GLP-1 agonists, including pharmaceutically acceptable salts and solvates thereof, and pharmaceutical compositions including the same.

WO2022031994 discloses compounds and pharmaceutical compositions thereof, for use in, e.g. treating type 2 diabetes mellitus, pre-diabetes, obesity, non-alc. fatty liver disease, non-alc. steatohepatitis, and cardiovascular disease.

CN114591308A discloses piperazine-imidazole containing GLP-1R receptor agonist compounds and application thereof.

WO2022111624 discloses benzimidazole derivatives that are agonists of a glucagon-like peptide-1 receptor (GLP-1R).

WO2022109182 discloses polyheterocyclic benzimidazole compounds and their preparation and use in the treatment of GLP-1R mediated diseases.

CN114478497A discloses a kind of aryl alkyl acid GLP-1 receptor agonist, its preparation method and application in treatment or prevention of GLP-1-mediated diseases and related diseases.

WO2022078380 discloses compounds that are GLP-1 agonists.

WO2022078407 discloses compounds that are GLP-1 agonists.

WO2022078152 discloses a kind of benzimidazolone compounds, their preparation method and application as GLP-1 receptor agonist.

CN114716423A discloses 5,6-dihydro-1,2,4-triazine compounds as GLP-1 receptor agonist.

CN114634510A discloses imidazolopyridine derivatives, which can be used to prepare drugs for treating GLP-1 receptor agonist mediated diseases.

CN114591296A discloses aromatic heterocyclic derivatives as GLP-1R agonists.

WO2022192430 discloses GLP-1R agonists and compositions, methods, and kits thereof.

WO2022192428 discloses GLP-1R agonists and compositions, methods, and kits thereof.

WO2022184849 discloses GLP-1R agonists, uses and pharmaceutical compositions thereof.

CN114907351A discloses tricyclic GLP-1 receptor agonists.

WO2022165076 discloses substituted benzimidazolecarboxylic acids which are GLP-1 receptor modulator compounds.

CN114805336A discloses fused imidazole compounds that are GLP-1 receptor agonists.

CN114763352A discloses benzimidazole derivatives and its application as GLP-1 receptor agonist.

WO2022199458 discloses thiophene GLP-1 receptor agonist compounds.

WO2022199661 discloses compounds that modulates the activity of GLP-1 receptor.

WO2022202864 discloses compounds that has GLP-1 receptor agonist activity.

WO2022216094 discloses compounds that has GLP-1 receptor agonist activity.

WO2022219495 discloses compounds that are activators of GLP-1.

WO2022235717 discloses benzimidazoyl GLP-1 receptor agonists.

WO2022225914 discloses carboxy-benzimidazole GLP-1 modulators.

WO2022225941 discloses carboxy-benzimidazole GLP-1 modulators.

J. Med. Chem. 2022, 65, 12, 8208-8226 discloses A Small-Molecule Oral Agonist of the Human Glucagon-like Peptide-1 Receptor.

Cell Research 2020, (39), 1140-1142 discloses structural insights into the activation of GLP-1R by a small molecule agonist.

An object is to provide novel GLP-1 receptor modulators useful in therapy. A further object is to provide novel compounds having improved safety profile, e.g with regards to selectivity for the GLP-1 receptor over e.g. phosphodiesterase 3 (PDE3) and/or having improved metabolic stability in the body.

SUMMARY

There is provided compounds that are modulators of the glucagon-like peptide-1 (GLP-1) receptor, their use as medicaments, pharmaceutical compositions containing them and synthetic routes to their production.

In one embodiment, there is provided a compound of Formula (I), (I)

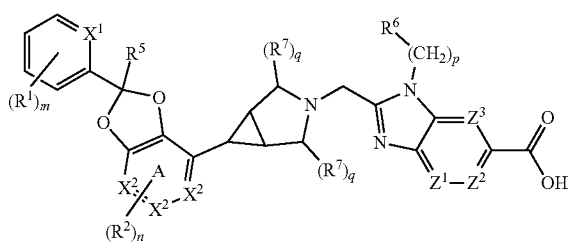

wherein $X^1$ is N or C;

$X^2$ is independently N or C, provided that no more than two atoms in the aromatic ring A are N;

$Z^1$ is N or $CR^3$;

$Z^2$ and $Z^3$ are each independently N or $CR^4$, provided that when $Z^1$ or $Z^3$ is N, $Z^2$ is $CR^4$;

$R^1$ is independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from H, $CH_3$, $CFH_2$, $CF_2H$ and $CF_3$;

$R^6$ is selected from (4- to 6-membered)heterocycloalkyl, (5- to 6-membered)heteroaryl, CN, $C_{1-4}$alkyl, O($C_{1-4}$ alkyl), S($C_{1-4}$alkyl), cyclopropyl, cyclobutyl, O(cyclopropyl) or S(cyclopropyl), wherein said (4- to 6-membered)heterocycloalkyl and (5- to 6-membered)heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

$R^7$ is independently selected from F, $C_{1-2}$alkyl and $OC_{1-2}$alkyl, wherein said $C_{1-2}$alkyl is substituted by 0, 1, 2 or 3 substituents independently selected from F;

m is 0, 1, 2 or 3;

n is 0 or 1;

p is 1, 2 or 3;

q is 0, 1 or 2;

or a pharmaceutically acceptable salt thereof.

The compounds of Formula (I) are modulators of the GLP-1 receptor. Thus, the compounds of Formula (I) can be used as a medicament, in particular for disorders, disease or conditions responsive to modulation of the GLP-1 receptor, and more specifically cardiovascular disease and metabolic conditions.

In another embodiment there is provided a compound of Formula (I), or a pharmaceutically acceptable salt of a compound of Formula (I), wherein the stereochemistry is undefined, e.g. a racemate or a mixture of diastereomers.

In another embodiment there is provided a compound of Formula (I), or a pharmaceutically acceptable salt of a compound of Formula (I), wherein the stereochemistry is defined.

In another embodiment there is provided a pharmaceutical formulation comprising a therapeutically effective amount of a compound of Formula (I), or a pharmaceutically acceptable salt of a compound of Formula (I), and a pharmaceutically acceptable diluent, excipient and/or inert carrier.

In a further embodiment there is provided a pharmaceutical formulation comprising a compound of Formula (I), or a pharmaceutically acceptable salt of a compound of Formula (I), for use in the treatment of a condition where modulation of the GLP-1 receptor would be beneficial.

In a further embodiment there is provided a compound of Formula (I), or a pharmaceutically acceptable salt of a compound of Formula (I), for use in therapy, especially in the treatment of cancer in a mammal, particularly a human.

In a further embodiment there is provided the use of a compound of Formula (I), or a pharmaceutically acceptable salt of a compound of Formula (I), for the manufacture of a medicament for the treatment of cardiovascular disease and metabolic conditions.

According to another aspect there is provided a process for the preparation of compounds of Formula (I), or pharmaceutically acceptable salts of compounds of Formula (I), and the intermediates used in the preparation thereof.

The compounds of Formula (I) described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

DETAILED DESCRIPTION

This detailed description and its specific examples, while indicating embodiments, are intended for purposes of illustration only. Therefore, there is no limitation to the illustrative embodiments described in this specification. In addition, it is to be appreciated that various features that are, for clarity reasons, described in the context of separate embodiments, also may be combined to form a single embodiment. Conversely, various features that are, for brevity reasons, described in the context of a single embodiment, also may be combined to form sub-combinations thereof.

Listed below are definitions of various terms used in the specification and claims.

It is to be understood that where in this specification a group is qualified by "defined above" the said group encompasses the first occurring and broadest definition as well as each and all of the other definitions for that group.

In this specification, the term "modulator" is used to describe a compound that exhibit varying receptor agonism, either full agonism, or partial agonism.

It is to be understood that in this specification "$C_{1-4}$" means a carbon group having 1, 2, 3 or 4 carbon atoms.

It is to be understood that in this specification "$C_{1-2}$" means a carbon group having 1 or 2 carbon atoms.

In this specification, unless stated otherwise, the term "alkyl" includes both straight and branched chain alkyl groups and may be, but is not limited to, methyl, ethyl, n-propyl, i-propyl, n-butyl, sec-butyl, iso-butyl or tert-butyl.

It is to be understood that in this specification "(5- to 6-membered)heteroaryl" means an aromatic ring with 5 to 6 atoms and containing one or more heteroatoms independently selected from nitrogen, oxygen or sulphur.

It is to be understood that in this specification "(6-membered)heteroaryl" means an aromatic ring with 6 atoms and containing one or more heteroatoms independently selected from nitrogen, oxygen or sulphur.

It is to be understood that in this specification "(6-membered)heteroaryl" means for example pyridine.

It is to be understood that in this specification "(5-membered)heteroaryl" means an aromatic ring with 5 atoms and containing one or more heteroatoms independently selected from nitrogen, oxygen or sulphur.

It is to be understood that in this specification "(4- to 6-membered)heterocycloalkyl" means a partially or completely saturated ring system with 4 to 5 atoms and wherein at least one of the ring carbon atoms is replaced with a heteroatom independently selected from nitrogen, oxygen or sulphur.

It is to be understood that in this specification a "heterocycloalkyl" substituent may be attached via a nitrogen atom having the appropriate valences, or via any ring carbon atom.

It is to be understood that in this specification a "heterocycloalkyl" or "heteroaryl" substituent may be further substituted, for example by a substituent selected from $C_{1-2}$alkyl.

In this specification, unless stated otherwise, the term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

There is provided compounds of Formula (I) wherein $X^1$, $X^2$, $Z^1$, $Z^2$, $Z^3$, $R^1$-$R^7$, m, n, p and q are as defined in Formula (I).

In one embodiment $X^1$ is N or C.

In a further embodiment $X^1$ is N.

In still a further embodiment $X^1$ is C.

$R^1$ is 0, 1, 2 or 3 substituents independently selected from F, Cl, Br, CN, $OCH_3$, $OCFH_2$, $OCF_2H$, $OCF_3$, $CH_3$, $CFH_2$, $CF_2H$ and $CF_3$.

In one embodiment $X^2$ is independently N or C, provided that no more than two atoms in the aromatic ring A are N.

In a further embodiment $X^2$ is C.

In one embodiment $Z^1$ is N or $CR^3$.

In a further embodiment $Z^1$ is N.

In still a further embodiment $Z^1$ is $CR^3$.

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F.

In one embodiment $Z^2$ and $Z^3$ are each independently N or $CR^4$, provided that when $Z^1$ or $Z^3$ is N, $Z^2$ is $CR^4$.

In a further embodiment $Z^1$ and $Z^2$ are N.

In still a further embodiment $Z^1$ and $Z^3$ are N.

In still a further embodiment $Z^2$ and $Z^3$ are N.

In still a further embodiment $Z^1$ is N, $Z^2$ and $Z^3$ are $CR^4$.

In still a further embodiment $Z^2$ is N, $Z^1$ and $Z^3$ are $CR^4$.

In still a further embodiment $Z^3$ is N, $Z^1$ and $Z^2$ are $CR^4$.

In still a further embodiment $Z^1$, $Z^2$ and $Z^3$ are $CR^4$.

$R^4$ is independently selected from H, F, Cl, OH, $CH_3$, $CFH_2$, $CF_2H$, $CF_3$, $OCH_3$, $OCFH_2$, $OCF_2H$ and $OCF_3$.

In one embodiment $R^1$ is 0, 1, 2 or 3 substituents independently selected from F, Cl, Br, CN, $OCH_3$, $OCFH_2$, $OCF_2H$, $OCF_3$, $CH_3$, $CFH_2$, $CF_2H$ and $CF_3$.

In a further embodiment $R^1$ is 0, 1 or 2 substituents independently selected from F, Cl, Br, CN, $OCH_3$, $OCFH_2$, $OCF_2H$, $OCF_3$, $CH_3$, $CFH_2$, $CF_2H$ and $CF_3$.

In still a further embodiment $R^1$ is 0, 1, 2 or 3 substituents independently selected from F, Cl, Br, CN, $OCH_3$.

In still a further embodiment $R^1$ is 0, 1 or 2 substituents independently selected from F, Cl, Br, CN, $OCH_3$.

In still a further embodiment $R^1$ is 0, 1 or 2 substituents independently selected from F, Cl and CN.

In still a further embodiment $R^1$ is 0 or 1 substituents selected from F, Cl and CN.

In one embodiment $R^2$ is selected from 0 or 1 F, Cl or CN.

In one embodiment $R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F.

In a further embodiment $R^3$ is selected from H, F, Cl, $C_{1-2}$alkyl and $OC_{1-2}$alkyl, wherein said $C_{1-2}$alkyl is substituted by 0, 1, 2 or 3 F.

In still a further embodiment $R^3$ is selected from H, F, Cl, $CH_3$, $CFH_2$, $CF_2H$, $CF_3$, $OCH_3$, $OCFH_2$, $OCF_2H$ and $OCF_3$.

In still a further embodiment $R^3$ is selected from H, F, Cl, $CH_3$ and $OCH_3$.

In one embodiment $R^4$ is independently selected from H, F, Cl, OH, $CH_3$, $CFH_2$, $CF_2H$, $CF_3$, $OCH_3$, $OCFH_2$, $OCF_2H$ and $OCF_3$.

In a further embodiment $R^4$ is independently selected from H, F, Cl, OH, $CH_3$ and $OCH_3$.

In still a further embodiment $R^4$ is independently selected from H, F, Cl, $CH_3$ and $OCH_3$.

In still a further embodiment $R^4$ is independently selected from H, F and Cl.

In one embodiment $R^5$ is selected from H, $CH_3$, $CFH_2$, $CF_2H$ and $CF_3$.

In a further embodiment $R^5$ is selected from H, and $CH_3$.

In still a further embodiment $R^5$ is $CH_3$.

In one embodiment $R^6$ is selected from (4- to 6-membered)heterocycloalkyl, (5- to 6-membered)heteroaryl, CN, $C_{1-4}$alkyl, $O(C_{1-4}alkyl)$, $S(C_{1-4}alkyl)$, cyclopropyl, cyclobutyl, O(cyclopropyl) or S(cyclopropyl), wherein said (4- to 6-membered)heterocycloalkyl and (5 to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F.

In a further embodiment $R^6$ is selected from $C_{1-4}$alkyl, $O(C_{1-4}alkyl)$ and $S(C_{1-4}alkyl)$, wherein said $C_{1-4}$alkyl is substituted by 0 or 1 substituent selected from CN or $OCH_3$, and 0, 1, 2 or 3 F.

In still a further embodiment $R^6$ is selected from cyclopropyl, cyclobutyl, O(cyclopropyl) or S(cyclopropyl), said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F.

In still a further embodiment $R^6$ is selected from (4- to 6-membered)heterocycloalkyl and (5 to 6-membered)heteroaryl, wherein said (4- to 6-membered)heterocycloalkyl and (5- to 6-membered)heteroaryl is substituted by 0 or 1 substituent selected from $C_{1-2}$alkyl.

In still a further embodiment $R^6$ is selected from (5- to 6-membered)heteroaryl, wherein said (5- to 6-membered) heteroaryl is substituted by 0 or 1 substituent selected from $C_{1-2}$alkyl.

In still a further embodiment $R^6$ is selected from (4- to 6-membered)heterocycloalkyl, wherein said (4- to 6-membered)heterocycloalkyl is substituted by 0 or 1 substituent selected from $C_{1-2}$alkyl.

In still a further embodiment $R^6$ is oxetan-2-yl.

In one embodiment $R^7$ is independently selected from F, $C_{1-2}$alkyl and $OC_{1-2}$alkyl, wherein said $C_{1-2}$alkyl is substituted by 0, 1, 2 or 3 substituents independently selected from F.

In a further embodiment $R^7$ is independently selected from F, $C_{1-2}$alkyl and $OC_{1-2}$alkyl.

In still a further embodiment $R^7$ is independently selected from F, $CH_3$ and $OCH_3$.

In one embodiment m is 0, 1, 2 or 3.

In a further embodiment m is 0, 1, or 2.

In still a further embodiment m is 1 or 2

In still a further embodiment m is 0 or 1.

In still a further embodiment m is 1.

In still a further embodiment m is 0.

In one embodiment n is 0 or 1.

In a further embodiment n is 1.

In still a further embodiment n is 0.

In one embodiment p is 1, 2 or 3.

In a further embodiment p is 1 or 2.

In still a further embodiment p is 1.

In one embodiment q is 0, 1 or 2.

In a further embodiment q is 0 or 1.

In still a further embodiment q is 0.

In one embodiment, there is provided a compound of Formula (Ia), (Ia)

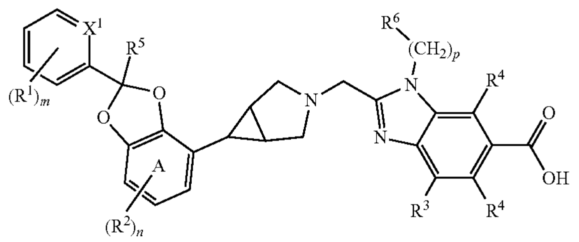

wherein $X^1$ is N or C;

$R^1$ is independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from H, $CH_3$, $CFH_2$, $CF_2H$ and $CF_3$;

$R^6$ is selected from (4- to 6-membered)heterocycloalkyl, (5- to 6-membered)heteroaryl, CN, $C_{1-4}$alkyl, $O(C_{1-4}$ alkyl), $S(C_{1-4}$alkyl), cyclopropyl, cyclobutyl, O(cyclopropyl) or S(cyclopropyl), wherein said (4- to 6-membered)heterocycloalkyl and (5- to 6-membered)heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

m is 0, 1, 2 or 3;

n is 0 or 1;

p is 1, 2 or 3;

or a pharmaceutically acceptable salt thereof.

In a further embodiment, there is provided a compound of Formula (Ia), wherein $X^1$ is N;

$R^1$ is independently selected from F, Cl and CN;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$ and $OCH_3$;

$R^5$ is selected from H, $CH_3$, $CFH_2$, $CF_2H$ and $CF_3$;

$R^6$ is selected from (4- to 6-membered)heterocycloalkyl, (5- to 6-membered)heteroaryl, CN, $C_{1-4}$alkyl, $O(C_{1-4}$ alkyl), $S(C_{1-4}$alkyl), cyclopropyl, cyclobutyl, O(cyclopropyl) or S(cyclopropyl), wherein said (4- to 6-membered)heterocycloalkyl and (5- to 6-membered)heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

m is 0, 1 or 2;

n is 0 or 1;

p is 1, 2 or 3;

or a pharmaceutically acceptable salt thereof.

In still a further embodiment, there is provided a compound of Formula (Ia), wherein $X^1$ is N;

$R^1$ is independently selected from F, Cl and CN;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$ and $OCH_3$;

$R^5$ is selected from H, $CH_3$, $CFH_2$, $CF_2H$ and $CF_3$;

$R^6$ is selected from (4- to 6-membered)heterocycloalkyl wherein said (4- to 6-membered)heterocycloalkyl is substituted by 0 or 1 substituent selected from $C_{1-2}$alkyl and;

m is 0, 1 or 2;

n is 0 or 1;

p is 1;

or a pharmaceutically acceptable salt thereof.

In one embodiment the compounds of Formula (I) are selected from:

2-(((1R,5S,6R)-6-(2-(4-Chloro-2-fluorophenyl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-((R*)-2-(4-chloro-2-fluorophenyl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, 2-(((1R,5S,6R)-6-(2-(5-Chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-((R*)-2-(5-Chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, 4-Chloro-2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-(2-(5-Chloropyridin-2-yl)-5-fluoro-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, 1-(2-(1H-Pyrazol-1-yl)ethyl)-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-4-fluoro-1H-benzo[d]imidazole-6-carboxylic acid, 4-Chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-((R*)-2-(5-Chloropyridin-2-yl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid, 2-(((1R,5S,6R)-6-((R*)-2-(5-Chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid, 2-(((1R,5S,6R)-6-((R*)-2-(4-Cyano-2-fluorophenyl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid, 4-Chloro-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-1H-benzo[d]imidazole-6-carboxylic acid, 2-(((1R,5S,6s)-6-((R*)-2-(5-Chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-methoxy-1H-benzo[d]imidazole-6-carboxylic acid, 2-(((1R,5S,6s)-6-((R*)-2-(5-Chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylic acid, 2-(((1R,5S,6s)-6-((R*)-2-(4-Chloro-2-fluorophenyl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylic acid, and pharmaceutically acceptable salts thereof.

It shall be noted that any one of these specific compounds may be disclaimed from any of the herein mentioned embodiments.

In one embodiment there is provided a process for the preparation of compounds of Formula (I), or pharmaceutically acceptable salts of compounds of Formula (I), and the intermediates used in the preparation thereof.

Another embodiment is a product obtainable by any of the processes or examples disclosed herein.

Medical and Pharmaceutical Use

The compounds of Formula (I) and their pharmaceutically acceptable salts are believed to be useful in the prevention or treatment of cardiovascular disease and metabolic conditions, including but not limited to type 2 diabetes (T2D), obesity, non-alcoholic fatty liver disease (NAFLD) and non-alcoholic steatohepatitis (NASH), in a mammal, particularly a human.

For the avoidance of doubt, as used herein, the term "treatment" includes therapeutic and/or prophylactic treatment.

When a compound or salt described herein is administered as therapy for treating a disorder, a "therapeutically effective amount" is an amount sufficient to reduce or completely alleviate symptoms or other detrimental effects of the disorder, cure the disorder, reverse, completely stop, or slow the progress of the disorder or reduce the risk of the disorder getting worse.

The compounds described herein are thus indicated both in the therapeutic and/or prophylactic treatment of these conditions.

The compounds described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

For the above-mentioned therapeutic indications, the dosage administered will vary with the compound employed, the mode of administration and the treatment desired. However, in general, satisfactory results are obtained when the compounds are administered at a dosage of the solid form of between 1 mg and 2000 mg per day.

The compounds of Formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect concerns a pharmaceutical composition comprising a novel compound of Formula (I), or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical Formulations are described in, for example, *Pharmaceuticals—The Science of Dosage Form Designs*, M. E. Aulton, Churchill Livingstone, $2^{nd}$ Ed. 2002. In one embodiment the pharmaceutical composition preferably comprises less than 80% and in another embodiment less than 50% of a compound of Formula (I), or a pharmaceutically acceptable salt thereof.

In one embodiment there is provided a compound selected from any one of the compounds of Formula (I), or a pharmaceutically acceptable salt of a compound of Formula (I), for use in therapy, especially in the prevention or treatment of cardiovascular disease and metabolic conditions, including but not limited to type 2 diabetes (T2D), obesity, non-alcoholic fatty liver disease (NAFLD) and non-alcoholic steatohepatitis (NASH).

These and other embodiments are described in greater detail herein below, where further aspects will be apparent to one skilled in the art from reading this specification.

Combination Therapy

The compounds of Formula (I), or pharmaceutically acceptable salts thereof, may also be administered in conjunction with other compounds used for the treatment of the above conditions.

In another embodiment, there is a combination therapy wherein a compound selected from any one of the compounds of Formula (I), or a pharmaceutically acceptable salt thereof, and a second active ingredient are administered concurrently, sequentially or in admixture, for the treatment of one or more of the conditions listed above. Such a combination may be used in combination with one or more further active ingredients.

When used in a combination therapy, it is contemplated that a compound selected from any one of the compounds of Formula (I), or pharmaceutically acceptable salts thereof, and the other active ingredients may be administered in a single composition, completely separate compositions, or a combination thereof. It also is contemplated that the active ingredients may be administered concurrently, simultaneously, sequentially, or separately.

The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

Pharmaceutical Compositions

There is provided a method of treatment of a condition where modulation of GLP-1 receptor is required, which method comprises administration of a therapeutically effective amount of a compound selected from any one of the compounds of Formula (I) to a person suffering from, or susceptible to, such a condition.

The compounds of Formula (I) will normally be administered via the oral, topical, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses. Conventional procedures for the selection and preparation of suitable pharmaceutical Formulations are described in, for example, *Pharmaceuticals—The Science of Dosage Form Designs*, M. E. Aulton, Churchill Livingstone, 2nd Ed. 2002.

In one embodiment suitable daily doses of the compounds of Formula (I) in therapeutical treatment of humans are about 0.0001-100 mg/kg body weight, in another embodiment 0.01-10 mg/kg body weight. The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the Formulation; and various other factors known to physicians and others skilled in the art.

According to a further aspect there is thus provided a pharmaceutical Formulation comprising a compound selected from any one of the compounds of Formula (I), or pharmaceutically acceptable derivatives thereof, in admixture with a pharmaceutically acceptable adjuvant, diluent and/or carrier.

The compound of Formula (I) may be present in the pharmaceutical Formulation in a concentration from 0.1 to 99.5%, such as from 0.5 to 95%, by weight of the total Formulation.

Preparation of the Compounds

The protection and deprotection of functional groups is described in *Protective Groups in Organic Synthesis*, 4th Ed, T. W. Greene and P. G. M. Wuts, Wiley-Interscience (2006) and *Protecting Groups*, 3rd Ed, P. J. Kocienski, Georg Thieme Verlag (2005).

A further embodiment encompasses pharmaceutically acceptable salts of the compounds of Formula (I).

A salt of a compound selected from any one of Formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

The term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Where the compound is sufficiently basic, pharmaceutically acceptable salts include, but are not limited to, inorganic or organic acid addition salts.

For reviews on suitable salts, see Berge et al., *J. Pharm. Sci.*, 1977, 66, 1-19 or *Handbook of Pharmaceutical Salts*: Properties, selection and use, P. H. Stahl, P. G. Vermuth, IUPAC, Wiley-VCH, 2002.

Where an acid co-former is a solid at r.t. and there is no or only partial proton transfer between the compound of Formula (I) and such an acid co-former, a co-crystal of the co-former and compound of Formula (I) may result rather than a salt. All such co-crystal forms of the compound of Formula (I) are encompassed herein.

It is also to be understood that certain compounds of Formula (I) may exist in solvated form, e.g. hydrates, including solvates of a pharmaceutically acceptable salt of a compound of Formula (I).

In a further embodiment, certain compounds of Formula (I) may exist as racemates and racemic mixtures, single enantiomers, individual diastereomers and diastereomeric mixtures. Certain compounds of Formula (I) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Stereoisomers may be separated using conventional techniques, e.g. chromatography or fractional crystallization, or the stereoisomers may be made by stereoselective synthesis.

In a further embodiment, the compounds of Formula (I) encompass any isotopically-labelled (or "radio-labelled") derivatives of a compound of Formula (I). Such a derivative is a derivative of a compound of Formula (I) wherein one or more atoms are replaced by an atom having an atomic mass or mass number different from the atomic mass or mass number typically found in nature. Examples of isotopes that may be incorporated include $^2H$ (also written as "D" for deuterium).

In a further embodiment, the compounds of Formula (I) may be administered in the form of a prodrug which is broken down in the human or animal body to give a compound of the Formula (I).

Various forms of prodrugs are known in the art. For examples of prodrug derivatives, see: *Nature Reviews Drug Discovery* 2008, 7, 255 and references cited therein.

Intermediate compounds may also exist in enantiomeric forms and may be used as purified enantiomers, diastereomers, racemates or mixtures.

EXAMPLES

The following examples are non-limiting examples.

General Conditions (i) operations were carried out at room temperature (rt), i.e. in the range 17 to 25° C. and under an atmosphere of an inert gas such as $N_2$ unless otherwise stated;

(ii) where reactions refer to being degassed or purged, this can be performed for example by purging the reaction solvent with a constant flow of nitrogen for a suitable period of time (for example 5 to 10 min) or by repeatedly evacuating the vessel and backfill with appropriate inert atmosphere (for example nitrogen (g) or argon (g));

(iii) where reactions refer to the use of a microwave reactor, one of the following microwave reactors were used: Biotage Initiator, Personal Chemistry Emrys Optimizer, Personal Chemistry Smith Creator or CEM Explorer;

(iv) in general, the course of reactions was followed by thin layer chromatography (TLC) and/or analytical high performance liquid chromatography (HPLC or UPLC) which was usually coupled to a mass spectrometer (LCMS).

(v) when necessary, organic solutions were dried over anhydrous $MgSO_4$ or $Na_2SO_4$, or by using ISOLUTE® Phase Separator, and work-up procedures were carried out using traditional phase separating techniques.

(vi), evaporations were carried out either by rotary evaporation in vacuo or in a Genevac HT-4/EZ-2 or Biotage V10;

(vii) unless otherwise stated, flash column chromatography was performed on straight phase silica, using either Merck Silica Gel (Art. 9385) or prep-packed cartridges such as Biotage® SNAP cartridges (40-63 m silica, 4-330 g), Biotage® Sfar Silica HC D cartridges (20 µm, 10-100 g), Interchim puriFlash™ cartridges (25 µm, 4-120 g), Interchim puriFlash™ cartridges (50 µm, 25-330 g), Grace™ GraceResolv™ Silica Flash Cartridges (4-120 g) or Agela Flash Colum Silica-CS cartridges (80-330 g), or on reversed phase silica using Agela Technologies C-18, spherical cartridges (20-35 µm, 100A, 80-330 g), manually or automated using a Grace Reveleris® X2 Flash system or similar system;

(viii) preparative reverse phase HPLC and preparative reverse phase SFC were performed using standard HPLC and SFC instruments, respectively, equipped with either a MS and/or UV triggered fraction collecting instrument, using either isocratic or a gradient of the mobile phase as described in the experimental section, and one of the following methods as described below;

HPLC Prep Methods:

PrepMethod A: The compound was purified by preparative HPLC on a Waters™ Sunfire™ C18 OBD column (5 µm, 100×19 mm ID) using a gradient of MeCN in $H_2O$ as mobile phase.

Relevant fractions were collected, combined and freeze-dried to give the purified compound or relevant fractions were collected, combined and concentrated at reduced pressure, extracted with DCM or EtOAc, and the organic phase was dried either over $Na_2SO_4$ or by using a phase-separator, and then concentrated at reduced pressure to give the purified compound.

(ix) chiral preparative chromatography was carried out using HPLC or SFC on a standard HPLC or SFC instruments, respectively, and using either isocratic or gradient run with mobile phase as described in the experimental section;

(x) yields, where present, are not necessarily the maximum attainable, and when necessary, reactions were repeated if a larger amount of the reaction product was required;

(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) in general, the structures of the end-products of the Formula (I) were confirmed by nuclear magnetic resonance (NMR) and/or mass spectral techniques; proton NMR chemical shift values were measured on the delta scale using Bruker Avance III 300, 400, 500 and 600 spectrometers, operating at $^1H$ frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. In certain instances, protons can be masked or partially masked by solvent peaks and will therefore either be missing and not reported or reported as multiplets overlapping with solvent. The following abbreviations have been used (and derivatives thereof, e.g. dd, doublet of doublets, ddd, doublet of doublet of doublets, dt, doublet of triplets, dq, doublet of quartet etc.): s, singlet; d, doublet; t, triplet; q, quartet; m, multiplet; br, broad; qn, quintet; p, pentet; h, heptet. In some cases, the structures of the end-products of the Formula (I) might appear as rotamers in the NMR-spectrum, in which instances only peaks of the major rotamer are reported. Electrospray mass spectral data were obtained using a Waters Acquity UPLC coupled to a Waters single quadrupole mass spectrometer or similar equipment, acquiring both positive and negative ion data, and generally, only ions relating to the parent structure are reported; high resolution electrospray mass spectral data were obtained using a Waters XEVO qToF mass spectrometer or similar equipment, coupled to a Waters Acquity UPLC, acquiring either positive and negative ion data, and generally, only ions relating to the parent structure are reported (xiii) intermediates were not necessarily fully purified but their structures and purity were assessed by TLC, analytical HPLC/UPLC, and/or NMR analysis and/or mass spectrometry;

(xiv) unless stated otherwise compounds containing an asymmetric carbon and/or sulfur atom were not resolved;

(xv) in general Examples and Intermediate compounds are named using ChemDraw Professional version 20.1.1 from PerkinElmer. ChemDraw Professional version 20.1.1 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules.

ChemDraw is optionally using labels in the graphical representation of stereocenters such as '&' and 'or' to describe the configuration of the stereochemical centers present in the structure.

In general chemical structures of Examples and Intermediates containing the label '&' at a stereocenter, means the configuration of such Example or Intermediate at that stereocenter is a mixture of both (R) and (S); and a label 'or' means the configuration of such Example or Intermediate at that stereocenter is either (S) or (R). Absolute, unspecified, '&', and 'or' stereocenters can all be present in a single structure.

In general for structures of Examples and Intermediates where all of the stereocenters are designated as '&', the structure is named with a "rac-" prefix. For structures of Examples and Intermediates where all of the stereocenters are designated as 'or', the structure is named with a "rel-" prefix.

In general Examples and Intermediate compounds are named using the descriptors (RS) and (SR) to denote general '&' centers for chemical structures with multiple chiral centers where only some are designated as '&'. The descriptors (R*) and (S*) are used to denote the general 'or' centers for chemical structures with multiple chiral centers where only some are designated as 'or'.

In general Examples and Intermediate compounds containing stereocenters having a relationship that is either cis or trans, are named using the descriptors (RS, SR) or (RS, RS), to denote chemical structures with multiple chiral centers where only some are designated as '&'.

In general the descriptors (r) and (s) are used to describe the absolute configuration of any pseudoasymmetric centers in the structures of Examples and Intermediates.

In general the label "Isomer 1" corresponds to the first eluted isomer, and "Isomer 2" corresponds to the second eluted isomer, on a given chiral HPLC column and eluent, and are used to distinguish two isomers containing one or more stereocenters with absolute unknown configuration;

(xvi) in addition to the ones mentioned above, the following abbreviations and units have been used:

ABBREVIATIONS aq aqueous
calcd calculated
DCM dichloromethane
DIPEA N,N-diisopropylethylamine
DMF N,N-dimethylformamide
DMSO dimethyl sulfoxide
ESI electrospray ionization
EtOAc ethyl acetate
FA formic acid
(g) gas
HPLC high performance liquid chromatography
HRMS high resolution mass spectrometry
ID inner diameter
IPA 2-methylpropan-ol
(l) liquid
LCMS liquid chromatography mass spectrometry
MeCN acetonitrile
MeOH methanol
MS mass spectrometry
MTBE tert-butyl methyl ether
NMR nuclear magnetic resonance
Pd(dppf)$Cl_2$·DCM [1,1'-Bis(diphenylphosphino)ferrocene]dichloropalladium(II) $CH_2Cl_2$ (1:1)
pTsOH para-toluenesulfonic acid
rt room temperature
(s) solid
sat saturated
SFC supercritical fluid chromatography
THE tetrahydrofuran
TLC thin layer chromatography
UPLC ultra performance liquid chromatography
UV ultraviolet Units atm atmosphere
C Celcius
g gram
h hour(s)
M mole per liter
mg milligram
MHz megaherz
min minute(s)
mL milliliter
mm millimeter
mol mole
mmol millimole(s)
μCi microcurie
μm micrometer
μmol micromole(s)
nm nanometer
ppm parts per million
W/v weight by volume

INTERMEDIATES

Intermediate 1 tert-Butyl (1R,5S,6s)-6-(2-(4-chloro-2-fluorophenyl)-2-methylbenzo[d][1,3]dioxol-4-yl)-3-azabicyclo[3.1.0]hexane-3-carboxylate Pd(dppf)$Cl_2$·DCM (183.14 mg, 224.26 μmol) was added to a suspension of 4-bromo-2-(4-chloro-2-fluorophenyl)-2-methylbenzo[d][1,3]dioxole (770 mg, 2.24 mmol), tert-butyl (1R,5S,6s)-6-(4,4,5,5-tetramethyl-1,3,2-dioxaborolan-2-yl)-3-azabicyclo[3.1.0]hexane-3-carboxylate (693 mg, 2.24 mmol) and $Cs_2CO_3$ (2.19 g, 6.73 mmol) in a mixture of 1,4-dioxane (60 mL) and water (15 mL), and the reaction mixture was stirred at 90° C. for 18 h. The reaction mixture was concentrated in vacuo and the residue was purified by flash chromatography on silica (hexane:MTBE, 90:10) to give the title compound (0.2 g, 65%) as a yellow oil; $^1$H NMR (500 MHz, $CDCl_3$) δ 7.52 (t, 1H), 7.20-7.08 (m, 2H), 6.72 (t, 1H), 6.65 (d, 1H), 6.43 (d, 1H), 3.83-3.22 (m, 4H), 2.05 (s, 3H), 1.94 (q, 2H), 1.74 (d, 1H), 1.48 (s, 9H).

Intermediate 2

(1R,5S,6s)-6-(2-(4-Chloro-2-fluorophenyl)-2-methylbenzo[d][1,3]dioxol-4-yl)-3-azabicyclo[3.1.0]hexane tert-Butyl (1R,5S,6s)-6-(2-(4-chloro-2-fluorophenyl)-2-methylbenzo[d][1,3]dioxol-4-yl)-3-azabicyclo[3.1.0]hexane-3-carboxylate Intermediate 1 (350 mg, 785 μmol) was treated with 4 M HCl in dioxane (15 mL) at rt and the reaction mixture was stirred for 18 h. The reaction mixture was concentrated at reduced pressure to give the hydrochloride of the title compound (0.241 g, 98%); MS (ESI) m/z $[M+H]^+$ 346.0.

Intermediate 3

Methyl 2-(((1R,5S,6R)-6-(2-(4-chloro-2-fluorophenyl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Methyl (S)-2-(chloromethyl)-1-(oxetan-2-ylmethyl)-1H-benzo[d]imidazole-6-carboxylate (317 mg, 1.08 mmol) was added to a suspension of (1R,5S,6s)-6-(2-(4-chloro-2-fluorophenyl)-2-methylbenzo[d][1,3]dioxol-4-yl)-3-azabicyclo[3.1.0]hexane hydrochloride Intermediate 2 (411 mg, 1.08 mmol) and DIPEA (695 mg, 5.38 mmol) in MeCN (40 mL), and the reaction mixture was stirred at 45° C. for 18 h. The reaction mixture was concentrated in vacuo, and the residue was diluted with water (20 mL). The mixture was extracted with DCM (3×10 mL), and the combined organic layer was dried over $Na_2SO_4$, filtered, and concentrated in vacuo. The residue was purified by flash chromatography on silica (chloroform:MTBE, 90:10) to give the title compound (0.179 g, 23%); MS (ESI) m/z $[M+H]^+$ 604.1.

Intermediate 4

Methyl (S)-3-methoxy-4-nitro-5-((oxetan-2-ylmethyl)amino)benzoate $K_2CO_3$ (5.43 g, 39.27 mmol) was added to a solution of methyl 3-fluoro-5-methoxy-4-nitrobenzoate (3 g, 13.09 mmol) and (S)-oxetan-2-ylmethanamine (1.14 g, 13.09 mmol) in THF:DMF (5:2, 110 mL) and the reaction mixture was stirred at 90° C. for 16 h. The solvent was removed under reduced pressure, and the residue was suspended in water (250 mL). The aqueous layer was extracted with EtOAc (3×250 mL), and the combined organic layer was dried over $Na_2SO_4$, filtered and evaporated at reduced pressure. The crude product was purified by flash column chromatography on silica (10-20% EtOAc in petroleum ether) to give the title compound (1.8 g, 46%) as a yellow solid; MS (ESI) m/z $[M+H]^+$ 297.1.

Intermediate 5

Methyl (S)-4-amino-3-methoxy-5-((oxetan-2-ylmethyl)amino)benzoate

A suspension of Pd—C(0.144 g, 1.35 mmol) and methyl (S)-3-methoxy-4-nitro-5-((oxetan-2-ylmethyl)amino)benzoate Intermediate 4 (4 g, 13.50 mmol) in THE (100 mL) was stirred under an atmosphere of $H_2$ (g) at 2 atm and 15° C. for 3 h. The reaction mixture was filtered through celite and the filter cake was washed with MeOH (3×300 mL). The filtrate was concentrated under reduced pressure. The crude product was purified by flash column chromatography on silica (50-70% EtOAc in petroleum ether) to give the title compound (3.00 g, 83%) as a light yellow solid; MS (ESI) m/z $[M+H]^+$ 267.3.

Intermediate 6

Methyl (S)-2-(chloromethyl)-4-methoxy-1-(oxetan-2-ylmethyl)-1H-benzo[d]imidazole-6-carboxylate pTsOH (0.119 g, 0.63 mmol) was added to a solution of methyl (S)-4-amino-3-methoxy-5-((oxetan-2-ylmethyl)amino)benzoate Intermediate 5 (0.333 g, 1.25 mmol) and 2-chloro-1,1,1-trimethoxyethane (0.387 g, 2.50 mmol) in MeCN (10 mL) and the reaction mixture was stirred at 45° C. for 30 min. The reaction mixture was concentrated under reduced pressure and the residue was purified by flash column chromatography on silica (50-100% EtOAc in heptane) to give the title compound (0.155 g, 38%); MS (ESI) m/z $[M+H]^+$ 325.0.

Intermediate 7

Methyl 2-(((1R,5S,6R)-6-(2-(4-chloro-2-fluorophenyl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate Methyl (S)-2-(chloromethyl)-4-methoxy-1-(oxetan-2-ylmethyl)-1H-benzo[d]imidazole-6-carboxylate Intermediate 6 (205 mg, 631 μmol) was added to a suspension of (1R,5S,6s)-6-(2-(4-chloro-2-fluorophenyl)-2-methylbenzo[d][1,3]dioxol-4-yl)-3-azabicyclo[3.1.0]hexane hydrochloride Intermediate 2 (241 mg, 631 μmol) and DIPEA (408 mg, 3.15 mmol) in MeCN (15 mL), and the reaction mixture was stirred at 45° C. for 18 h. The reaction mixture was concentrated in vacuo, and the residue was diluted with water (20 mL) and the mixture was extracted with DCM. The combined organic layer was dried over $Na_2SO_4$, filtered, and concentrated in vacuo. The residue was purified by preparative HPLC, PrepMethod A, (gradient: 10-35%), to give the title compound (221 mg, 28%); MS (ESI) m/z $[M+H]^+$ 634.2.

Intermediate 8

Methyl 2-(((1R,5S,6R)-6-((R*)-2-(4-chloro-2-fluorophenyl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate. Isomer 2

The stereoisomers of methyl 2-(((1R,5S,6R)-6-(2-(4-chloro-2-fluorophenyl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate Intermediate 7 were separated by chiral chromatography on a Chiralcel OD-H column (250×30 mm, 5 μm), eluted with hexane/IPA/MeOH (70/15/15), at a flow rate of 30 mL/min; the second eluted peak was collected and evaporated to give the title compound Isomer 2 Intermediate 8 (48 mg); MS (ESI) m/z $[M+H]^+$ 634.2.

Intermediate 9 tert-Butyl (1R,5S,6s)-6-(2-(5-chloropyridin-2-yl)-2-methylbenzo[d][1,3]dioxol-4-yl)-3-azabicyclo[3.1.0]hexane-3-carboxylate Pd(dppf)$Cl_2$·DCM (381 mg, 466 μmol) was added to a suspension of 2-(4-bromo-2-methylbenzo[d][1,3]dioxol-2-yl)-5-chloropyridine (1.52 g, 4.66 mmol), tert-butyl (1R,5S,6s)-6-(4,4,5,5-tetramethyl-1,3,2-dioxaborolan-2-yl)-3-azabicyclo[3.1.0]hexane-3-carboxylate (1.44 g, 4.66 mmol) and $Cs_2CO_3$ (4.56 g, 13.99 mmol) in 1,4-dioxane (120 mL) and water (20 mL), and the reaction mixture was stirred at 90° C. for 18 h. The reaction mixture was concentrated in vacuo and the residue was purified by flash chromatography on silica (hexane:MTBE, 85:15) to give the title compound (0.45 g, 35%) as a yellow gummy oil; MS (ESI) m/z $[M-1+H]^+$ 373.2 (product minus tert-butyl)

Intermediate 10

(1R,5S,6s)-6-(2-(5-Chloropyridin-2-yl)-2-methylbenzo[d][1,3]dioxol-4-yl)-3-azabicyclo[3.1.0]hexane tert-Butyl (1R,5S,6s)-6-(2-(5-chloropyridin-2-yl)-2-methylbenzo[d][1,3]dioxol-4-yl)-3-azabicyclo[3.1.0]hexane-3-carboxylate Intermediate 9 (0.45 g, 1.05 mmol) was treated with 4 M HCl in 1,4-dioxane (10 mL) at rt, and the reaction mixture was stirred for 18 h. The reaction mixture was concentrated at reduced pressure to give the hydrochloride of the title compound (0.34 g, 98%); MS (ESI) m/z $[M+H]^+$ 329.0.

Intermediate 11

Methyl 2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Methyl (S)-2-(chloromethyl)-1-(oxetan-2-ylmethyl)-1H-benzo[d]imidazole-6-carboxylate (356 mg, 1.21 mmol) was added to a suspension of (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (442 mg, 1.21 mmol) and DIPEA (782 mg, 6.05 mmol) in MeCN (40 mL), and the reaction mixture was stirred at 45° C. for 18 h. The reaction mixture was concentrated in vacuo, the residue was diluted with water (20 mL), and the mixture was extracted with DCM (3×5 mL). The combined organic layer was dried over $Na_2SO_4$, filtered, and concentrated in vacuo. The residue was purified by flash chromatography on silica (chloroform:MTBE, 80:20) to give the title compound (0.37 g, 52%); MS (ESI) m/z $[M+H]^+$ 587.2.

Intermediate 12

Methyl 2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate Methyl (S)-2-(chloromethyl)-4-methoxy-1-(oxetan-2-ylmethyl)-1H-benzo[d]imidazole-6-carboxylate Intermediate 6 (421 mg, 1.30 mmol) was added to a suspension of (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (474 mg, 1.30 mmol) and DIPEA (838 mg, 6.48 mmol) in MeCN (45 mL) and the reaction mixture was stirred at 45° C. for 18 h. The reaction mixture was concentrated in vacuo, the residue was diluted with water (20 mL) and the mixture was extracted with DCM. The combined organic layer was dried over $Na_2SO_4$, filtered, and concentrated in vacuo. The residue was purified by preparative HPLC, PrepMethod A, (gradient: 40-65%) to give the title compound (323 mg, 40%); MS (ESI) m/z $[M+H]^+$ 617.4.

Intermediate 13

Methyl 2-((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate, Isomer 1

Intermediate 14

Methyl 2-(((1R,5S,6R)-6-(R*)-2-(5-chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate, Isomer 2

The stereoisomers of methyl 2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate Intermediate 12 were separated by chiral chromatography on a Chiralpak IG column (5 μm, 250×20 mm ID), eluted with hexane/IPA/MeOH (70/15/15) at a flow rate of 21 mL/min;

the first eluted compound was collected and evaporated to give the title compound Isomer 1 Intermediate 13 (206 mg); MS (ESI) m/z $[M+H]^+$ 617.4; and the second eluted compound was collected and evaporated to give the title compound Isomer 2 Intermediate 14 (149 mg); MS (ESI) m/z $[M+H]^+$ 617.4.

Intermediate 15

(S)-5-Bromo-3-chloro-2-nitro-N-(oxetan-2-ylmethyl)aniline

DIPEA (15.44 mL, 88.43 mmol) and 5-bromo-1-chloro-3-fluoro-2-nitrobenzene (7.5 g, 29.48 mmol) were added dropwise to a solution of (S)-oxetan-2-ylmethanamine (2.57 g, 29.48 mmol) in THE (200 mL), and the reaction mixture was stirred at 60° C. for 3 h. The reaction mixture was diluted with EtOAc (300 mL) and washed with sat brine (4×300 mL). The organic layer was dried over $Na_2SO_4$, filtered and evaporated. The crude product was purified by flash chromatography on silica (0-50% EtOAc in petroleum ether) to give the title compound (9.00 g, 95%) as a yellow oil; MS (ESI) m/z $[M+H]^+$ 321/323.

Intermediate 16

(S)-5-Bromo-3-chloro-$N^1$-(oxetan-2-ylmethyl)benzene-1,2-diamine

Fe (s) (24.66 g, 441.60 mmol) was added to a mixture of (S)-5-bromo-3-chloro-2-nitro-N-(oxetan-2-ylmethyl)aniline Intermediate 15 (14.2 g, 44.16 mmol) and $NH_4Cl$ (23.62 g, 441.60 mmol) in MeOH (400 mL) and water (100 mL) at 20° C., and the reaction mixture was stirred at 60° C. for 6 h. The reaction mixture was filtered and the precipitates were washed with MeOH (4×100 mL). The filtrate was concentrated under reduced pressure and the crude product was diluted with EtOAc (500 mL). The organic layer was washed sequentially with water (500 mL) and sat brine (500 mL), dried over $Na_2SO_4$, filtered and evaporated. The crude product was purified by flash chromatography on silica (30-50% EtOAc in petroleum ether) to give the title compound (12.00 g, 93%) as a white solid; MS (ESI) m/z $[M+H]^+$ 292/291.

Intermediate 17

Methyl (S)-4-amino-3-chloro-5-((oxetan-2-ylmethyl)amino)benzoate

A mixture of (S)-5-bromo-3-chloro-$N^1$-(oxetan-2-ylmethyl)benzene-1,2-diamine Intermediate 16 (1.5 g, 5.14 mmol), Pd(dppf)$Cl_2$·DCM (0.38 g, 0.51 mmol) and DIPEA (8.99 mL, 51.45 mmol) in MeOH (300 mL) was stirred under an atmosphere of CO(g) at 60 atm and 120° C. for 30 h. The solvent was removed under reduced pressure and the crude product was purified by flash chromatography on silica (20-25% EtOAc in petroleum ether) to give the title compound (1.0 g, 72%) as a white solid; MS (ESI) m/z $[M+H]^+$ 271.

Intermediate 18

Methyl (S)-4-chloro-2-(chloromethyl)-1-(oxetan-2-ylmethyl)-1H-benzo[d]imidazole-6-carboxylate pTsOH (0.357 g, 1.88 mmol) was added to a solution of methyl (S)-4-amino-3-chloro-5-((oxetan-2-ylmethyl)amino) benzoate Intermediate 17 (5.08 g, 18.77 mmol) and 2-chloro-1,1,1-trimethoxyethane (3.77 g, 24.40 mmol) in MeCN (20 mL) and the reaction mixture was stirred at 50° C. for 30 min. 2-Chloro-1,1,1-trimethoxyethane (1.16 g, 7.51 mmol) was added and the reaction mixture was stirred at 50° C. for 20 min. The reaction mixture was diluted with EtOAc (10 mL) and extracted with $NaHCO_3$ (aq, 2×3 mL). The organic layer was dried over $MgSO_4$, filtered and concentrated at reduced pressure. The crude compound was purified by flash chromatography on silica (50-100% EtOAc in heptane) to give the title compound (5.30 g, 86%); MS (ESI) m/z $[M+H]^+$ 329.1.

Intermediate 19

Methyl 4-chloro-2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Methyl (S)-4-chloro-2-(chloromethyl)-1-(oxetan-2-ylmethyl)-1H-benzo[d]imidazole-6-carboxylate Intermediate 18 (306 mg, 0.93 mmol) was added to a suspension of (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (340 mg, 0.93 mol) and DIPEA (601 mg, 4.0 mmol) in MeCN (7 mL), and the reaction mixture was stirred at 45° C. for 18 h. The reaction mixture was concentrated in vacuo, the residue was diluted with water (20 mL), and the mixture was extracted with DCM. The combined organic layer was dried over $Na_2SO_4$, filtered, and concentrated in vacuo. The residue was purified by preparative HPLC, PrepMethod A, (gradient: 0-50%) to give the title compound (0.106 g, 53%); MS (ESI) m/z $[M+H]^+$ 623.2.

Intermediate 20

Methyl 4-chloro-2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Isomer 1

The stereoisomers of methyl 4-chloro-2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Intermediate 19 were separated by chiral chromatography on a Chiralpak IB column (5 μm, 250×20 mm ID), eluted with hexane:IPA:MeOH (95:2.5:2.5), at a flow rate of 21 mL/min;

the first eluted compound was collected and evaporated to give the title compound Isomer 1 Intermediate 20 (118 mg); MS (ESI) m/z $[M+H]^+$ 621.2.

Intermediate 21

2-(4-Bromo-5-fluoro-2-methylbenzo[d][1,3]dioxol-2-yl)-5-chloropyridine

A mixture of 3-bromo-4-fluorobenzene-1,2-diol (16.34 g, 78.94 mmol), 5-chloro-2-ethynylpyridine (10.86 g, 78.94 mmol), and $Ru_3(CO)_{12}$ (1.26 g, 1.97 mmol) in toluene (250 mL) was degassed for 1 min and then heated at 100° C. for 16 h. The reaction mixture was concentrated at reduced pressure, and the residue was purified by flash chromatography on silica (hexane:MTBE, 90:10) to give the title compound (14 g, 50%); $^1$H NMR (400 MHz, $CDCl_3$) δ 8.62 (d, 1H), 7.70 (dd, 1H), 7.57 (d, 1H), 6.66 (dd, 1H), 6.58 (t, 1H), 2.09 (s, 3H).

Intermediate 22 tert-Butyl (1R,5S,6s)-6-(2-(5-chloropyridin-2-yl)-5-fluoro-2-methylbenzo[d][1,3]dioxol-4-yl)-3-azabicyclo[3.1.0]hexane-3-carboxylate Pd(dppf)$Cl_2$·DCM (731 mg, 895 μmol) was added to a suspension of 2-(4-bromo-5-fluoro-2-methylbenzo[d][1,3] dioxol-2-yl)-5-chloropyridine Intermediate 21 (3.08 g, 8.95 mmol), tert-butyl (1R,5S,6s)-6-(4,4,5,5-tetramethyl-1,3,2-dioxaborolan-2-yl)-3-azabicyclo[3.1.0]hexane-3-carboxylate (2.77 g, 8.95 mmol) and $Cs_2CO_3$ (8.75 g, 26.85 mmol) in 1,4-dioxane (60 mL) and water (15 mL), and the reaction mixture was stirred at 90° C. for 18 h. The reaction mixture was concentrated in vacuo and the residue was purified by flash chromatography on silica (hexane:MTBE, 85:15) to give the title compound (2.05 g, 55%) as a yellow oil; MS (ESI) m/z $[M+H]^+$ 391.

Intermediate 23

(1R,5S,6s)-6-(2-(5-Chloropyridin-2-yl)-5-fluoro-2-methylbenzo[d][1,3]dioxol-4-yl)-3-azabicyclo[3.1.0] hexane tert-Butyl (1R,5S,6s)-6-(2-(5-chloropyridin-2-yl)-5-fluoro-2-methylbenzo[d][1,3]dioxol-4-yl)-3-azabicyclo [3.1.0]hexane-3-carboxylate Intermediate 22 (933 mg, 2.09 mmol) was treated with 4 M HCl in 1,4-dioxane (15 mL) at rt, and the reaction mixture was stirred for 18 h. The reaction mixture was concentrated at reduced pressure to give the hydrochloride salt of the title compound (0.8 g, quantitative yield); MS (ESI) m/z $[M+H]^+$ 347.0.

Intermediate 24

Methyl 2-(((1R,5S,6R)-6-(2-(5-chloropyridin-2-yl)-5-fluoro-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate Methyl (S)-2-(chloromethyl)-4-methoxy-1-(oxetan-2-ylmethyl)-1H-benzo[d]imidazole-6-carboxylate Intermediate 6 (582 mg, 1.80 mol) was added to a suspension of (1R,5S,6s)-6-(2-(5-chloropyridin-2-yl)-5-fluoro-2-methylbenzo[d][1,3]dioxol-4-yl)-3-azabicyclo[3.1.0]hexane hydrochloride Intermediate 23 (694 mg, 1.80 mmol) DIPEA (1.14 g, 9.0 mmol) MeCN (10 mL) and the reaction mixture was stirred at 45° C. for 18 h. The reaction mixture was concentrated in vacuo, the residue was diluted with water (20 mL), and the mixture was extracted with DCM. The combined organic layer was dried over $Na_2SO_4$, filtered, and concentrated in vacuo. The residue was purified by preparative HPLC, PrepMethod A, (gradient: 40-65%), to give the title compound (0.56 g, 53%); MS (ESI) m/z $[M+H]^+$ 635.2.

Intermediate 25

Methyl 3-((2-(1H-pyrazol-1-yl)ethyl)amino)-5-fluoro-4-nitrobenzoate

A mixture of methyl 3,5-difluoro-4-nitrobenzoate (2.5 g, 11.51 mmol), 2-(1H-pyrazol-1-yl)ethan-1-amine (1.28 g, 11.51 mmol) and DIPEA (2.98 g, 23.03 mmol) in THE (15 mL) was heated under stirring at 45° C. for 16 h. The reaction mixture was cooled to rt and diluted with water and the mixture was extracted with MTBE. The combined organic layer was washed with water and brine, dried over $Na_2SO_4$, and filtered. The filtrate was concentrated in vacuo to give the title compound (3.5 g, 46% purity) as orange solid which was used in the next step without additional purification; MS (ESI) m/z 309.0.

Intermediate 26

Methyl 3-((2-(1H-pyrazol-1-yl)ethyl)amino)-4-amino-5-fluorobenzoate

10% Pd/C (0.35 g, 0.57 mmol) was added to a solution of crude methyl 3-((2-(1H-pyrazol-1-yl)ethyl)amino)-5-fluoro-4-nitrobenzoate Intermediate 25 (3.5 g) in MeOH (25 mL) and the suspension was stirred under an atmosphere of $H_2$ (g) at 1 atm and rt for 24 h. The reaction mixture was filtered, and the filtrate was concentrated in vacuo. The residue was purified by flash chromatography on silica (0-95% MeCN in chloroform) to give the title compound (1.2 g, 38%); MS (ESI) m/z $[M+H]^+$ 279.0.

Intermediate 27

Methyl 1-(2-(1H-pyrazol-1-yl)ethyl)-4-fluoro-2-(hydroxymethyl)-1H-benzo[d]imidazole-6-carboxylate 2,2,2-Triethoxyethan-1-ol (576 mg, 3.23 mmol) followed by pTSOH (93 mg, 539 μmol) were added to a solution of methyl 3-((2-(1H-pyrazol-1-yl)ethyl)amino)-4-amino-5-fluorobenzoate Intermediate 26 (300 mg, 1.08 mmol) in MeCN (7 mL), and the reaction mixture was heated at 60° C. for 1 h. The reaction mixture was allowed to cool to rt and stirred at this temperature for an additional 16 h. The formed slurry precipitate was filtered off and the obtained solid was dried in vacuo to give the title compound (300 mg, 87%); MS (ESI) m/z 319.2.

Intermediate 28

Methyl 1-(2-(1H-pyrazol-1-yl)ethyl)-2-(chloromethyl)-4-fluoro-1H-benzo[d]imidazole-6-carboxylate A catalytic amount of DMF was added to a solution methyl 1-(2-(1H-pyrazol-1-yl)ethyl)-4-fluoro-2-(hydroxymethyl)-1H-benzo[d]imidazole-6-carboxylate Intermediate 27 (300 mg, 942 μmol) in DCM (10 mL), followed by a dropwise addition of $SOCl_2$ (560 mg, 4.71 mmol) under vigorous stirring. The reaction mixture was stirred at rt for 1 h and then concentrated in vacuo, to give the title compound as the hydrochloride salt (300 mg, 95%) as dark red solid; MS (ESI) m/z $[M+H]^+$ 337.0.

Intermediate 29

Methyl 1-(2-(1H-pyrazol-1-yl)ethyl)-2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-4-fluoro-1H-benzo[d]imidazole-6-carboxylate Methyl 1-(2-(1H-pyrazol-1-yl)ethyl)-2-(chloromethyl)-4-fluoro-1H-benzo[d]imidazole-6-carboxylate hydrochloride Intermediate 28 (101 mg, 300 μmol) was added to a suspension of (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (110 mg, 300 μmol) and DIPEA (194 mg, 1.5 mmol) in MeCN (10 mL), and the reaction mixture was stirred at rt for 18 h. The reaction mixture was concentrated in vacuo, the residue was diluted with water (20 mL), and the mixture was extracted with EtOAc. The organic layer was dried over $Na_2SO_4$, filtered, and concentrated in vacuo. The residue was purified by preparative HPLC, PrepMethod A, (gradient: 20-50%), to give the title compound (116 mg, 87%); MS (ESI) m/z $[M+H]^+$ 629.2.

Intermediate 30

Methyl 1-(2-(1H-pyrazol-1-yl)ethyl)-2-((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-4-fluoro-1H-benzo[d]imidazole-6-carboxylate Isomer 2

The stereoisomers of methyl 1-(2-(1H-pyrazol-1-yl)ethyl)-2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-4-fluoro-1H-benzo[d]imidazole-6-carboxylate Intermediate 29 were separated by chiral chromatography on a Chiralpak IB column (5 μm, 250×21 mm ID), eluted with $CO_2$-MeOH (70:30), at a flow rate of 50 mL/min;

The second eluted compound was collected and evaporated to give the title compound Isomer 2 Intermediate 30 (42 mg); MS (ESI) m/z $[M+H]^+$ 629.0.

Intermediate 31

Methyl 4-chloro-2-(((1R,5S,6R)-6-(2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Methyl (S)-4-chloro-2-(chloromethyl)-1-(oxetan-2-ylmethyl)-1H-benzo[d]imidazole-6-carboxylate Intermediate 18 (386 mg, 1.17 mmol). was added to a suspension of (1R,5S,6s)-6-(2-(5-chloropyridin-2-yl)-5-fluoro-2-methylbenzo[d][1,3]dioxol-4-yl)-3-azabicyclo[3.1.0]hexane Intermediate 23 (449 mg, 1.17 mmol) and DIPEA (758 mg, 5.86 mmol) in MeCN (50 mL), and the reaction mixture was stirred at 45° C. for 18 h. The reaction mixture was concentrated in vacuo, the residue was diluted with water (20 mL), and the mixture was extracted with DCM. The combined organic layer was dried over $Na_2SO_4$, filtered, and concentrated in vacuo. The residue was purified by preparative HPLC, PrepMethod A, (gradient: 15-35%) to give the title compound (541 mg, 72%); MS (ESI) m/z $[M+H]^+$ 639.2.

Intermediate 32

Methyl 4-chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Isomer 1

Intermediate 33

Methyl 4-chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Isomer 2

The stereoisomers of methyl 4-chloro-2-(((1R,5S,6R)-6-(2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Intermediate 31 were separated by chiral chromatography on a Chiralpak IF column (5 μm, 250×20 mm ID), eluted with $CO_2$-MeOH, (70:30), at a flow rate of 50 mL/min;

the first eluted compound was collected and evaporated to give the title compound Isomer 1, Intermediate 32 (138 mg); MS (ESI) m/z $[M+H]^+$ 639.2; and the second eluted compound was collected and evaporated to give the title compound Isomer 2 Intermediate 33 (150 mg); MS (ESI) m/z $[M+H]^+$ 639.2.

Intermediate 34

Methyl (S)-3-fluoro-4-nitro-5-((oxetan-2-ylmethyl)amino)benzoate

DIPEA (11.90 g, 0.092 mol) was added to a solution of methyl 3,5-difluoro-4-nitrobenzoate (10 g, 0.046 mol) in THE (100 mL), and the reaction mixture was stirred for 10 min. A solution of (S)-oxetan-2-ylmethanamine (4.01 g, 0.046 mol) in THF (20 mL) was added, and the reaction mixture was stirred at 25° C. for 16 h. EtOAc (20 mL) was added to the reaction mixture, and the mixture was filtered through silica gel. The filter cake was rinsed with EtOAc and the combined filtrates were concentrated at reduced pressure and at 45° C., to give the title compound (12 g, 92%); MS (ESI) m/z $[M+H]^+$ 285.0.

Intermediate 35

Methyl (S)-4-amino-3-fluoro-5-((oxetan-2-ylmethyl)amino)benzoate

Methyl (S)-3-fluoro-4-nitro-5-((oxetan-2-ylmethyl)amino)benzoate Intermediate 34 (12 g, 0.042 mol) was dissolved in THE (100 mL) and treated with 10% Pd/C (1.2 g). The reaction mixture was stirred under an atmosphere of $H_2$ (g) at ambient pressure and temperature for 24 h. The reaction mixture was filtered, and the filtrate was concentrated at reduced pressure. The residue was purified by flash chromatography on silica (0-95% MeCN in chloroform) to give the title compound (8.5 g, 79%); MS (ESI) m/z $[M+H]^+$ 255.0.

Intermediate 36

Methyl (S)-2-(chloromethyl)-4-fluoro-1-(oxetan-2-ylmethyl)-1H-benzo[d]imidazole-6-carboxylate 2-Chloro-1,1,1-trimethoxyethane (3.64 g, 0.023 mol, 3.18 ml) and pTSOH (127 mg, 669 μmol) was added to a solution of methyl (S)-4-amino-3-fluoro-5-((oxetan-2-ylmethyl)amino)benzoate Intermediate 35 (5 g, 0.019 mol) in THE (50 mL), and the reaction mixture was stirred at 50° C. overnight. The reaction mixture was poured into water and the mixture was extracted with EtOAc. The organic layer was washed with brine and concentrated in vacuo to give the title compound (6 g, 95%); MS (ESI) m/z $[M+H]^+$ 285.0.

Intermediate 37

Methyl 2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Methyl (S)-2-(chloromethyl)-4-fluoro-1-(oxetan-2-ylmethyl)-1H-benzo[d]imidazole-6-carboxylate Intermediate 36 (310 mg, 0.992 mmol) was added to a suspension of (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (362 mg, 0.992 mmol) and DIPEA (641 mg, 4.958 mmol) in MeCN (20 mL), and the reaction mixture was stirred at 45° C. for 18 h. The reaction mixture was concentrated in vacuo, the residue was diluted with water (20 mL), and the mixture was extracted with DCM. The organic layer was dried over $Na_2SO_4$, filtered, and concentrated in vacuo. The residue was purified by preparative HPLC, PrepMethod A, (gradient: 15-35%) to give the title compound (209 mg, 35%); MS (ESI) m/z $[M+H]^+$ 605.2.

Intermediate 38

Methyl 2-((S)((R*)-2-(5-chloropyridin-2-yl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 2

The stereoisomers of methyl 2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Intermediate 37 were separated by chiral chromatography on a Chiralcel OD-H column (5 μm, 250×20 mm ID), eluted with hexane:IPA:MeOH (80:10:10), at a flow rate of 21 mL/min;

the second eluted compound was collected and evaporated to give the title compound Isomer 2 Intermediate 38 (109 mg); MS (ESI) m/z $[M+H]^+$ 605.4.

Intermediate 39

Methyl 2-(((1R,5S,6R)-6-(2-(5-chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Methyl (S)-2-(chloromethyl)-4-fluoro-1-(oxetan-2-ylmethyl)-1H-benzo[d]imidazole-6-carboxylate Intermediate 36

(251 mg, 0.80 mmol) was added to a suspension of (1R,5S,6s)-6-(2-(5-chloropyridin-2-yl)-5-fluoro-2-methylbenzo[d][1,3]dioxol-4-yl)-3-azabicyclo[3.1.0]hexane hydrochloride Intermediate 23 (308 mg, 0.80 mmol) and DIPEA (519 mg, 4.01 mmol) in MeCN (25 mL) and the reaction mixture was stirred at 45° C. for 18 h. The reaction mixture was concentrated in vacuo, the residue was diluted with water (20 mL), and the mixture was extracted with DCM. The organic layer was dried over $Na_2SO_4$, filtered, and concentrated in vacuo. The residue was purified by preparative HPLC, PrepMethod A, (gradient: 40-50%), to give the title compound (197 mg, 39%); MS (ESI) m/z $[M+H]^+$ 623.2.

Intermediate 40

Methyl 2-(1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 1

Intermediate 41

Methyl 2-(1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 2

The stereoisomers of methyl 2-(((1R,5S,6R)-6-(2-(5-chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Intermediate 39 were separated by chiral chromatography on a Chiralpak AD-H-III column (5 μm, 250×30 mm ID), eluted with hexane:IPA:MeOH (90:5:5), at a flow rate of 12 mL/min;

the first eluted compound was collected and evaporated to give the title compound Isomer 1 Intermediate 40 (80 mg); MS (ESI) m/z $[M+H]^+$ 623.0; and the second eluted compound was collected and evaporated to give the title compound Isomer 2 Intermediate 41 (84 mg); MS (ESI) m/z [M+H]623.0.

Intermediate 42

Methyl 3-chloro-5-(((1-ethyl-1H-imidazol-5-yl)methyl)amino)-4-nitrobenzoate

A mixture of methyl 3-chloro-5-fluoro-4-nitrobenzoate (7.93 g, 33.95 mmol), (1-ethyl-1H-imidazol-5-yl)methanamine (4.25 g, 33.95 mmol) and DIPEA (10.97 g, 84.87 mmol) in DMF (80 mL) was heated at 50° C. for 16 h. The reaction mixture was poured into water (100 mL) and filtered. The precipitate was collected and dried to give the title compound (11.5 g) as a dark yellow solid; MS (ESI) m/z $[M+H]^+$ 325.6.

Intermediate 43

Methyl 4-amino-3-chloro-5-(((1-ethyl-1H-imidazol-5-yl)methyl)amino)benzoate

Wet Pt/C (1%, 1.99 g, 10.2 mmol) was added to a suspension of methyl 3-chloro-5-(((1-ethyl-1H-imidazol-5-yl)methyl)amino)-4-nitrobenzoate Intermediate 42 (11.52 g, 34.01 mmol) in MeOH (100 mL) and the reaction mixture was stirred under an atmosphere of $H_2$ (g) at 1 atm and at 20° C. for 16 h. The reaction mixture was filtered, and the solids were washed with MeOH (50 mL). The filtrate was concentrated under reduced pressure. The crude product was purified by straight phase flash chromatography on silica (0-40% MeOH in $CHCl_3$) to give the title compound (4 g, 38%); $^1H$ NMR (400 MHz, $CDCl_3$): δ 7.59 (s, 1H), 7.58 (s, 1H), 7.28 (s, 1H), 6.68 (s, 1H), 4.5 (br s, 1H), 4.24 (s, 2H), 3.99-3.97 (q, 2H), 3.85 (s, 3H), 1.43 (t, 3H).

Intermediate 44

Methyl 4-chloro-2-(chloromethyl)-1-((1-ethyl-1H-imidazol-5-yl)methyl)-1H-benzo[d]imidazole-6-carboxylate Step a) Methyl 4-chloro-((1-ethyl-1H-imidazol-5-yl)methyl)-2-(hydroxymethyl)-1H-benzo[d]imidazole-6-carboxylate 2,2,2-Triethoxyethan-1-ol (3.11 g, 17.46 mmol) and pTsOH (100 mg, 582 μmol) were added to a stirred solution of methyl 4-amino-3-chloro-5-(((1-ethyl-1H-imidazol-5-yl)methyl)amino)benzoate Intermediate 43 (1.8 g, 5.82 mmol) in MeCN (100 mL) and the reaction mixture was heated at 60° C. 18 h. The reaction mixture was concentrated under reduced pressure, and the crude residue was diluted with EtOAc. The organic layer was washed with water and $NaHCO_3$ (aq), dried and evaporated at reduced pressure to give the crude subtitle compound (2.04 g, 60% purity); MS (ESI) m/z $[M+H]^+$ 349.2.

Step b) Methyl 4-chloro-2-(chloromethyl)-1-((1-ethyl-1H-imidazol-5-yl)methyl)-1H-benzo[d]imidazole-6-carboxylate Methyl 4-chloro-1-((1-ethyl-1H-imidazol-5-yl)methyl)-2-(hydroxymethyl)-1H-benzo[d]imidazole-6-carboxylate Step a) (2.04 g, 5.85 mmol) was added in portions to a vigorously stirred mixture of $SOCl_2$ (6.97 g, 58.55 mmol) and DMF (one drop). After complete addition the reaction mixture was stirred at rt for 1 h, and then concentrated at reduced pressure to give the hydrochloride of the title compound (1.8 g, 71%) as a white solid; MS (ESI) m/z $[M+H]^+$ 367.2.

Intermediate 45

Methyl 3-(((1-ethyl-1H-imidazol-5-yl)methyl)amino)-5-methoxy-4-nitrobenzoate

A solution of methyl 3-fluoro-5-methoxy-4-nitrobenzoate (1.4 g, 6.11 mmol) in DMF (5 mL) was added dropwise to a solution (1-ethyl-1H-imidazol-5-yl)methanamine dihydrochloride (1.33 g, 6.72 mmol) and DIPEA (3.95 g, 30.54 mmol) in DMF (5 mL) and the reaction mixture was heated under stirring at 60° C. for 16 h. The reaction mixture was cooled to rt, diluted with water (30 mL), and the mixture was extracted with DCM (3×30 mL). The combined organic layer was washed with brine (50 mL) and water (50 mL), dried over $Na_2SO_4$, filtered, and concentrated in vacuo. The crude product was purified by straight phase flash chromatography on silica (10% EtOAc in hexane) to give the title compound (1.9 g, 93%) as a yellow solid; MS (ESI) m/z $[M+H]^+$ 335.1.

Intermediate 46

Methyl 4-amino-3-(((1-ethyl-1H-imidazol-5-yl) methyl)amino)-5-methoxybenzoate

10% Pd/C (0.2 g) was added to a solution of methyl 3-(((1-ethyl-1H-imidazol-5-yl)methyl)amino)-5-methoxy-4-nitrobenzoate Intermediate 45 (1.9 g, 5.0 mmol) in MeOH (20 mL), and the reaction mixture was stirred under an atmosphere of $H_2$(g) (1 atm) at rt for 36 h. The reaction mixture was filtered through a pad of celite, the filtrate was concentrated in vacuo, and the crude product was purified by straight phase flash chromatography on silica (0-95% MeOH in MTBE) to give the title compound (1.5 g, 87%) as a yellow solid; MS (ESI) m/z $[M+H]^+$ 305.2.

Intermediate 47

Methyl 1-((1-ethyl-1H-imidazol-5-yl)methyl)-2-(hydroxymethyl)-4-methoxy-1H-benzo[d]imidazole-6-carboxylate 2,2,2-Triethoxyethan-1-ol (2.63 g, 14.78 mmol) and pTsOH (424 mg, 2.46 mmol) were added to a solution of methyl 4-amino-3-(((1-ethyl-1H-imidazol-5-yl)methyl) amino)-5-methoxybenzoate Intermediate 46 (1.5 g, 4.93 mmol) in MeCN (7 mL), and the reaction mixture was heated under stirring at 60° C. for 1 h. The reaction mixture cooled to rt and concentrated in vacuo, and the residue was purified by straight phase flash chromatography on silica (0-95% MeOH in MTBE) to give the title compound (1.4 g, 75%); $^1$H NMR (400 MHz, DMSO-$d_6$) δ 7.74 (s, 1H), 7.65 (s, 1H), 7.26 (s, 1H), 6.52 (s, 1H), 5.75 (s, 1H), 5.65 (s, 2H), 4.70 (d, 2H), 3.95 (d, 5H), 3.83 (s, 3H), 1.11 (t, 3H).

Intermediate 48

Methyl 2-(chloromethyl)-1-((1-ethyl-1H-imidazol-5-yl)methyl)-4-methoxy-1H-benzo[d]imidazole-6-carboxylate A catalytic amount of DMF followed by $SOCl_2$ (2.42 g, 20.32 mmol) were added dropwise under vigorous stirring to a solution of methyl 1-((1-ethyl-1H-imidazol-5-yl)methyl)-2-(hydroxymethyl)-4-methoxy-1H-benzo[d]imidazole-6-carboxylate Intermediate 47 (1.4 g, 4.07 mmol) in DCM (20 mL), and the reaction mixture was stirred at rt for 1 h. The reaction mixture was concentrated in vacuo and the obtained solid was dried in vacuo to give the dihydrochloride salt of the title compound (1.70 g, 96%) as a beige solid; MS (ESI) m/z $[M+H]^+$ 363.2.

Intermediate 49

Methyl 2-(chloromethyl)-1-((1-ethyl-1H-imidazol-5-yl)methyl)-4-fluoro-1H-benzo[d]imidazole-6-carboxylate The title compound was prepared in four steps from methyl 3,5-di-fluoro-4-nitrobenzoate (2.0 g, 9.2 mmol) in analogy with the description of Intermediate 48 to give the hydrochloride of the title compound (1.06 g, 96%) as a brown solid; MS (ESI) m/z $[M+H]^+$ 351.

Intermediate 50

4-(4-((1R,5S,6s)-3-Azabicyclo[3.1.0]hexan-6-yl)-2-methylbenzo[d][1,3]dioxol-2-yl)-3-fluorobenzonitrile The title compound was prepared from 4-(4-bromo-2-methylbenzo[d][1,3]dioxol-2-yl)-3-fluorobenzonitrile WO2020207474 (382 mg, 1.15 mmol) and tert-butyl (1R,5S,6s)-6-(4,4,5,5-tetramethyl-1,3,2-dioxaborolan-2-yl)-3-azabicyclo[3.1.0]hexane-3-carboxylate (425 mg, 1.37 mmol) in analogy with the description for Intermediate 22. The reaction mixture was concentrated in vacuo and the residue was purified by straight phase flash chromatography on silica (EtOAc:hexane, 10:90) to give the Boc-protected intermediate of the title compound (326 mg, 87%), $^1$H NMR (400 MHz, $CDCl_3$) δ 7.70 (t, 1H), 7.50-7.37 (m, 2H), 6.72 (t, 1H), 6.64 (d, 1H), 6.43 (d, 1H), 3.71 (dd, 2H), 3.48 (d, 2H), 2.10-2.03 (m, 3H), 1.91 (s, 2H), 1.73 (s, 1H), 1.46 (s, 9H). The Boc-protected intermediate was treated with TFA (1 eq) in DCM at rt for 18 h. The reaction mixture was concentrated at reduced pressure to give the TFA salt of the title compound (456 mg, quantitative yield).

Intermediate 51

Methyl 2-(((1R,5S,6R)-6-(2-(4-cyano-2-fluorophenyl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Methyl (S)-2-(chloromethyl)-4-fluoro-1-(oxetan-2-ylmethyl)-1H-benzo[d]imidazole-6-carboxylate Intermediate 36 (316 mg, 1.01 mmol) was added to a suspension of 4-(4-((1R,5S,6s)-3-azabicyclo[3.1.0]hexan-6-yl)-2-methylbenzo[d][1,3]dioxol-2-yl)-3-fluorobenzonitrile Intermediate 50 (340 mg, 1.01 mmol) and DIPEA (785 mg, 6.07 mmol) in MeCN (25 mL) and the reaction mixture was stirred at 45° C. for 18 h. The reaction mixture was concentrated in vacuo, and the residue was diluted with water (20 mL) and extracted with DCM. The combined organic layers were dried over $Na_2SO_4$, filtered, and concentrated in vacuo. The residue was purified by preparative HPLC, PrepMethod A (gradient: 50-75%), to give the title compound (265 mg, 43%); MS (ESI) m/z $[M+H]^+$ 613.0.

Intermediate 52

Methyl 2-(((1R,5S,6R)-6-((R*)-2-(4-cyano-2-fluorophenyl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 2

The stereoisomers of methyl 2-(((1R,5S,6R)-6-(2-(4-cyano-2-fluorophenyl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Intermediate 51 were separated by chiral chromatography on a Chiralcel OD-H column (250×20 mm, 5 μm), eluted with hexane/IPA/MeOH (60/20/20), at a flow rate of 12 mL/min; the second eluted peak was collected and evaporated to give the title compound Isomer 2 Intermediate 52 (102 mg); MS (ESI) m/z $[M+H]^+$ 613.0.

Intermediate 53

Methyl 4-chloro-2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-1H-benzo[d]imidazole-6-carboxylate NaI (8.2 mg, 54.7 μmol) and $K_2CO_3$ (378 mg, 2.74 mmol) was added to a stirred solution of methyl 4-chloro-2-(chloromethyl)-1-((1-ethyl-1H-imidazol-5-yl)methyl)-1H-benzo[d]imidazole-6-carboxylate dihydrochloride Intermediate 44 (723 mg, 1.64 mmol) and (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (200 mg, 548 μmol) in DMF (10 mL) and the reaction mixture was heated at 60° C. for 14 h. The reaction mixture was poured into water, and the mixture was extracted with EtOAc (3×60 mL). The combined organic layer was washed with brine (100 mL), dried over anhydrous $Na_2SO_4$, filtered, and concentrated in vacuo. The residue was purified by preparative HPLC, PrepMethod A (gradient: 40-65%), to give the title compound (57 mg, 16%); MS (ESI) m/z $[M+H]^+$ 659.0.

Intermediate 54

Methyl 4-chloro-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-1H-benzo[d]imidazole-6-carboxylate Isomer 1

The stereoisomers of methyl 4-chloro-2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-1H-benzo[d]imidazole-6-carboxylate Intermediate 53 were separated by chiral chromatography on a Chiralpak AD-H-V column (250×20 mm, 5 μm), eluted with hexane:IPA:MeOH (80:10:10), at a flow rate of 13 mL/min; the first eluted peak was collected and evaporated to give the title compound Isomer 1 Intermediate 54 (23 mg); MS (ESI) m/z $[M+H]^+$ 661.2.

Intermediate 55

Methyl 2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-methoxy-1H-benzo[d]imidazole-6-carboxylate Methyl 2-(chloromethyl)-1-((1-ethyl-1H-imidazol-5-yl)methyl)-4-methoxy-1H-benzo[d]imidazole-6-carboxylate dihydrochloride Intermediate 48 (0.702 g, 1.6 mmol) was added to a suspension of (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (0.588 g, 1.6 mmol), DIPEA (1.249 g, 9.6 mmol) and NaI (0.965 g, 6.4 mmol) in DMF (35 mL) and the reaction mixture was stirred at 60° C. for 18 h. The reaction mixture was poured into water (50 mL) and extracted with DCM (3×25 mL). The combined organic layer was dried over $Na_2SO_4$, filtered, and concentrated under reduced pressure. The residue was purified by preparative HPLC, PrepMethod A (gradient: 40-65%), to give the title compound (233 mg, 23%); MS (ESI) m/z $[M+H]^+$ 657.2.

Intermediate 56

Methyl 2-((((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-methoxy-1H-benzo[d]imidazole-6-carboxylate Isomer 1

The stereoisomers of methyl 2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-methoxy-1H-benzo[d]imidazole-6-carboxylate Intermediate 55 were separated by chiral chromatography on a Chiralpak IB column (250×20 mm, 5 μm), eluted with IPA:MeOH (50:50), at a flow rate of 12 mL/min;

the first eluted peak was collected and evaporated to give the title compound Isomer 1 Intermediate 56 (69 mg); MS (ESI) m/z $[M+H]^+$ 657.2.

Intermediate 57

Methyl 2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate A mixture of (1R,5S,6s)-6-(2-(5-chloropyridin-2-yl)-2-methylbenzo[d][1,3]dioxol-4-yl)-3-azabicyclo[3.1.0]hexane hydrochloride Intermediate 10 (400 mg, 1.1 mmol), DIPEA (707 mg, 5.47 mmol), and methyl 2-(chloromethyl)-1-((1-ethyl-1H-imidazol-5-yl)methyl)-4-fluoro-1H-benzo[d]imidazole-6-carboxylate dihydrochloride Intermediate 49 (928 mg, 2.2 mmol) in MeCN (5 mL) was heated at 50° C. for 16 h. The reaction mixture was cooled, diluted with water, and extracted with EtOAc (3×5 mL). The combined organic layer was washed with brine, dried over anhydrous $Na_2SO_4$, and filtered. The filtrate was concentrated in vacuo and the residue was purified by preparative HPLC, PrepMethod A, (gradient: 40-65%), to give the title compound (120 mg, 17%); MS (ESI) m/z $[M+H]^+$ 643.2.

Intermediate 58

Methyl 26-(((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate Isomer 1

The stereoisomers of methyl 2-(((1R,5S,6s)-6-(2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate Intermediate 57 were separated by chiral chromatography on a Chiralpak IB column (250×20 mm, 5 μm), eluted with IPA:MeOH (50:50), at a flow rate of 11 mL/min;

the first eluted peak was collected and evaporated to give the title compound Isomer 1 Intermediate 58 (51 mg); MS (ESI) m/z $[M+H]^+$ 643.0.

Intermediate 59

Methyl 2-(((1R,5S,6s)-6-(2-(4-chloro-2-fluorophenyl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate A mixture of (1R,5S,6s)-6-(2-(4-chloro-2-fluorophenyl)-2-methylbenzo[d][1,3]dioxol-4-yl)-3-azabicyclo[3.1.0]

hexane hydrochloride Intermediate 2 (435 mg, 1.14 mmol), DIPEA (735 mg, 5.69 mmol) and methyl 2-(chloromethyl)-1-((1-ethyl-1H-imidazol-5-yl)methyl)-4-fluoro-1H-benzo[d]imidazole-6-carboxylate dihydrochloride Intermediate 49 (964 mg, 2.28 mmol) in MeCN (3 mL) was heated at 50° C. for 16 h. The reaction mixture was cooled, diluted with water, and extracted with EtOAc (3×10 mL). The combined organic layer was washed with brine, dried over anhydrous $Na_2SO_4$, and filtered. The filtrate was concentrated under reduced pressure and the residue was purified by preparative HPLC, PrepMethod A (gradient: 40-65%), to give the title compound (38 mg, 4.3%); MS (ESI) m/z $[M+H]^+$ 660.2.

Intermediate 60

Methyl 2-(((1R,5S,6s)-6-((R*)-2-(4-chloro-2-fluorophenyl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate Isomer 2

The stereoisomers of methyl 2-(((1R,5S,6s)-6-(2-(4-chloro-2-fluorophenyl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate Intermediate 59 were separated by chiral chromatography on a Chiralpak IB column (250×20 mm, 5 μm), eluted with IPA:MeOH (50:50), at a flow rate of 10 mL/min;

the second eluted peak was collected and evaporated to give the title compound Isomer 2 Intermediate 60 (15 mg); MS (ESI) m/z $[M+H]^+$ 660.2.

EXAMPLES

Example 1

2-(((1R,5S,6R)-6-(2-(4-Chloro-2-fluorophenyl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid

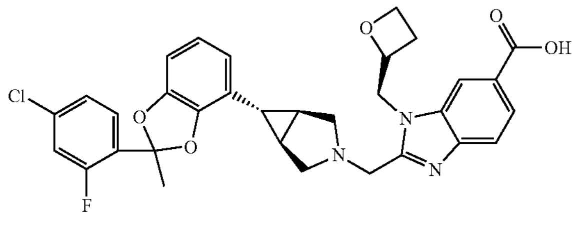

LiOH monohydrate (19 mg, 445 μmol) was added to a solution of methyl 2-(((1R,5S,6R)-6-(2-(4-chloro-2-fluorophenyl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Intermediate 3 (179 mg, 297 μmol) in a mixture of THF:$H_2O$ (1:1, 20 mL) and the reaction mixture was stirred at rt for 24 h. The reaction mixture was concentrated under reduced pressure, and the resulting solution was acidified to pH 3 using 5% citric acid (aq). The formed precipitate was filtered off and the obtained solid was dried in vacuo to give the title compound (0.14 g, 86%); HRMS (ESI) m/z $[M+H]^+$ calcd for $C_{32}H_{30}ClFN_3O_5$: 590.1852, found: 590.1864; $^1H$ NMR (500 MHz, DMSO-$d_6$) δ 12.45 (s, 1H), 8.27 (s, 1H), 7.78 (d, 1H), 7.63 (d, 1H), 7.54 (t, 2H), 7.33 (d, 1H), 6.71 (d, 2H), 6.44 (dd, 1H), 5.04 (d, 1H), 4.72 (dd, 1H), 4.56 (d, 1H), 4.49-4.29 (m, 2H), 4.12 (s, 1H), 3.92 (s, 1H), 3.14 (d, 1H), 3.02 (d, 1H), 2.78-2.55 (m, 4H), 2.18 (s, 1H), 2.01 (s, 3H), 1.84 (s, 2H).

Example 2

2-(((1R,5S,6R)-6-((R*)-2-(4-Chloro-2-fluorophenyl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid Isomer 2

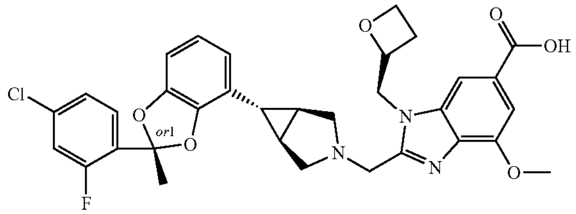

Isomer 2

LiOH monohydrate (8 mg, 0.19 mmol) was added to a solution of methyl 2-(((1R,5S,6R)-6-((R*)-2-(4-chloro-2-fluorophenyl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate, Isomer 2 Intermediate 8 (48 mg, 0.077 mmol) in a mixture of THF:$H_2O$ (2:1, 5 mL) and the reaction mixture was stirred at rt for 16 h. The reaction mixture was acidified using a solution of $NaH_2PO_4$ (aq), diluted with water and the mixture was extracted with EtOAc. The organic layer was dried over $Na_2SO_4$ and concentrated at reduced pressure. The residue was purified by preparative HPLC, PrepMethod A, (gradient: 10-50%), to give the title compound (35 mg, 66%); HRMS (ESI) m/z $[M+H]^+$ calcd for $C_{33}H_{32}ClFN_3O_6$: 620.1958, found: 620.1992; $^1H$ NMR (600 MHz, DMSO-$d_6$) δ 12.75 (s, 1H), 7.90 (d, 1H), 7.59-7.48 (m, 2H), 7.33 (dd, 1H), 7.24 (d, 1H), 6.71 (q, 2H), 6.44 (dd, 1H), 5.03 (qd, 1H), 4.67 (dd, 1H), 4.53 (dd, 1H), 4.45 (td, 1H), 4.34 (dt, 1H), 4.05 (d, 1H), 3.94 (s, 3H), 3.88 (d, 1H), 3.08 (d, 1H), 2.95 (d, 1H), 2.77-2.66 (m, 1H), 2.65-2.53 (m, 2H), 2.40 (ddd, 1H), 2.16 (d, 1H), 2.00 (s, 3H), 1.83 (ddt, 2H).

Example 3

2-(((1R,5S,6R)-6-(2-(5-Chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid

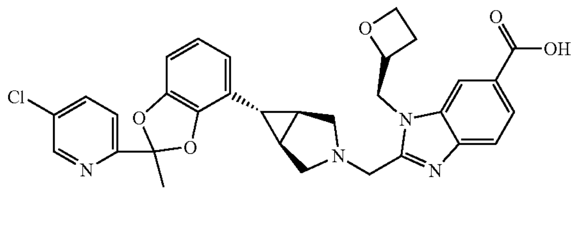

LiOH monohydrate (40 mg, 942 μmol) was added to a solution of methyl 2-(((1R,5S,6R)-6-(2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Intermediate 11 (369 mg, 628 μmol) in a mixture of THF:$H_2O$ (1:1, 20 mL) and the reaction mixture was stirred at rt for 24 h. The reaction mixture was concentrated under reduced pressure and the resulting solution was acidified to pH 3.0 using 5% citric acid (aq). The formed precipitate was filtered off and the solid obtained was dried in vacuo to give the title compound (0.29 g, 80%); HRMS (ESI) m/z $[M+H]^+$ calcd for $C_{31}H_{30}ClN_4O_5$: 573.1900, found: 573.1908; $^1H$ NMR (500 MHz, DMSO-$d_6$) δ 12.42 (s, 1H), 8.70 (s, 1H), 8.26 (s, 1H), 7.99 (d, 1H), 7.78 (d, 1H), 7.70-7.50 (m, 2H), 6.72 (d, 2H), 6.43 (d, 1H), 5.00 (d, 1H), 4.68 (dd, 1H), 4.53 (d, 1H), 4.49-4.26 (m, 2H), 4.16 (d, 1H), 3.91 (s, 1H), 3.17 (d, 1H), 2.98 (d, 1H), 2.76-2.57 (m, 3H), 2.18 (s, 1H), 1.99 (s, 3H), 1.85 (s, 3H).

Example 4a 2-(((1R,5S,6R)-6-((R*)-2-(5-Chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, Isomer 1

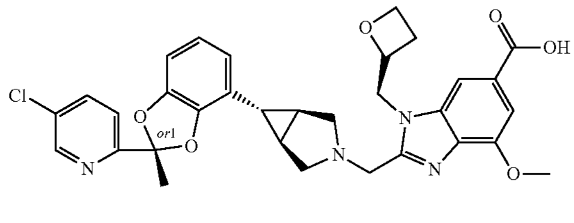

Isomer 1

LiOH monohydrate (35 mg, 0.82 mmol) was added to a solution of methyl 2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate, Isomer 1 Intermediate 13 (206 mg, 0.33 mmol) in a mixture of THF:$H_2O$ (2:1, 15 mL), and the reaction mixture was stirred at rt for 16 h. The reaction mixture was acidified to pH 3 with 1 M citric acid (aq), diluted with water, and extracted with EtOAc. The organic layer was dried over $Na_2SO_4$, filtered and concentrated at reduced pressure. The residue was purified by preparative HPLC, PrepMethod A, (gradient: 0-45%) to give the title compound (118 mg, 87%) as a white solid; HRMS (ESI) m/z $[M+H]^+$ calcd for $C_{32}H_{32}ClN_4O_6$: 603.2004, found: 603.2020; $^1H$ NMR (600 MHz, DMSO-$d_6$) δ 12.73 (s, 1H), 8.70 (d, 1H), 7.99 (dd, 1H), 7.88 (s, 1H), 7.59 (d, 1H), 7.23 (s, 1H), 6.76-6.66 (m, 2H), 6.44 (d, 1H), 4.99 (dd, 1H), 4.64 (dd, 1H), 4.50 (dd, 1H), 4.43-4.29 (m, 2H), 4.08 (s, 1H), 3.93 (s, 3H), 3.83 (d, 1H), 3.19-3.06 (m, 1H), 2.89 (s, 1H), 2.74-2.56 (m, 3H), 2.43-2.31 (m, 1H), 2.16 (d, 1H), 1.99 (s, 3H), 1.84 (d, 2H).

Example 4b 2-(((1R,5S6R)-6-((R*)-2-(5-Chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, Isomer 2

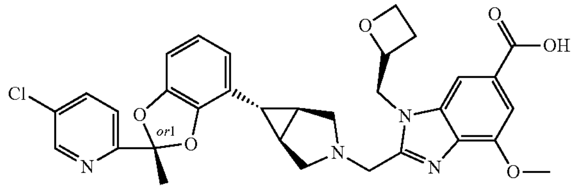

Isomer 2

LiOH monohydrate (25 mg, 0.60 mmol) was added to a solution of methyl 2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate, Isomer 2 Intermediate 14 (149 mg, 0.24 mmol) in a mixture of THF:$H_2O$ (2:1, 15 mL), and the reaction mixture was stirred at rt for 16 h. The reaction mixture was acidified to pH 3 with 1 M citric acid (aq), diluted with water, and extracted with EtOAc. The organic layer was dried over $Na_2SO_4$, filtered and concentrated at reduced pressure. The residue was purified by preparative HPLC, PrepMethod A, (gradient: 0-45%) to give the title compound (108 mg, 85%) as a white solid; HRMS (ESI) m/z $[M+H]^+$ calcd for $C_{32}H_{32}ClN_4O_6$: 603.2004, found: 603.2034; $^1H$ NMR (600 MHz, DMSO-$d_6$) δ 12.16 (s, 1H), 8.69 (s, 1H), 7.98 (d, 1H), 7.88 (s, 1H), 7.58 (d, 1H), 7.24 (s, 1H), 6.71 (dt, 2H), 6.44 (d, 1H), 5.02 (d, 1H), 4.64 (dd, 1H), 4.50 (d, 1H), 4.44 (q, 1H), 4.32 (q, 1H), 4.03 (d, 1H), 3.94 (s, 3H), 3.85 (d, 1H), 3.07 (d, 1H), 2.94 (d, 1H), 2.74-2.56 (m, 4H), 2.15 (s, 1H), 1.99 (s, 3H), 1.83 (d, 2H).

Example 5

4-Chloro-2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, Isomer 1

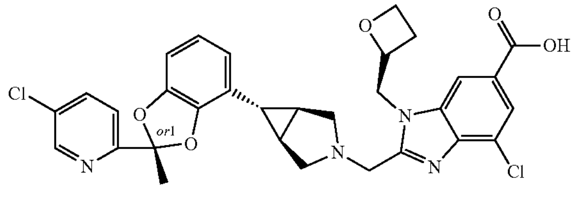

Isomer 1

LiOH monohydrate (20 mg, 0.47 mmol) was added to a solution of methyl 4-chloro-2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Isomer 1 Intermediate 20 (118 mg, 0.19 mmol) in a mixture THF:$H_2O$ (2:1, 10 mL), and the reaction mixture was stirred at rt for 16 h. The reaction mixture was acidified to pH 3 with 1 M citric acid (aq), diluted with water, and extracted with EtOAc. The organic layer was dried over $Na_2SO_4$ and concentrated at reduced pressure. The residue was purified by preparative HPLC, PrepMethod A, (gradient 0-50%) to give the title compound (92 mg, 87%) as a white solids; HRMS (ESI) m/z $[M+H]^+$ calcd for $C_{31}H_{29}Cl_2N_4O_5$: 607.1510, found: 607.1548; $^1H$ NMR (600 MHz, DMSO-$d_6$) δ 12.75 (br s, 1H) 8.70 (d, 1H), 8.23 (s, 1H), 7.99 (dd, 1H), 7.77 (s, 1H), 7.58 (d, 1H), 6.71 (dt, 2H), 6.44 (d, 1H), 5.03 (dt, 1H), 4.72 (dd, 1H), 4.56 (dd, 1H), 4.44 (q, 1H), 4.35 (dt, 1H), 4.09 (d, 1H), 3.90 (d, 1H), 3.09 (d, 1H), 2.94 (d, 1H), 2.71 (p, 1H), 2.66-2.54 (m, 2H), 2.42-2.35 (m, 1H), 2.15 (t, 1H), 1.99 (s, 3H), 1.83 (ddt, 2H).

Example 6

2-(((1R,5S,6R)-6-(2-(5-Chloropyridin-2-yl)-5-fluoro-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid

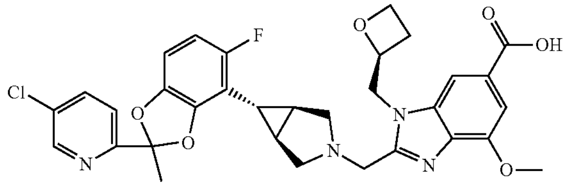 [SMILES: COc1cc(C(=O)O)cc2c1nc(CN1C[C@@H]3[C@H](C1)[C@H]3c1c(F)ccc3c1OC(C)(c1ccc(Cl)cn1)O3)n2C[C@@H]1CCO1]

LiOH monohydrate (92 mg, 2.20 mmol) was added to a solution of of methyl 2-(((1R,5S,6R)-6-(2-(5-chloropyridin-2-yl)-5-fluoro-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylate Intermediate 24 (0.56 g, 0.88 mmol) in a mixture of THF:$H_2O$ (2:1, 10 mL) and the reaction mixture was stirred at rt for 16 h. The reaction mixture was acidified to pH 3 with 1 M citric acid (aq), diluted with water and extracted with EtOAc. The organic layer was dried over $Na_2SO_4$ and concentrated at reduced pressure. The residue was purified by preparative HPLC, PrepMethod A, (gradient: 0-50%) to give the title compound (0.5 g, 92%) as a white solid; HRMS (ESI) m/z $[M+H]^+$ calcd for $C_{32}H_{31}ClFN_4O_6$: 621.1910, found: 621.1952; $^1H$ NMR (600 MHz, DMSO-$d_6$) δ 12.65 (s, 1H), 8.70 (t, 1H), 7.99 (dt, 1H), 7.88 (s, 1H), 7.59 (dd, 1H), 7.24 (s, 1H), 6.77-6.44 (m, 2H), 5.00 (dt, 1H), 4.65 (dd, 1H), 4.51 (dd, 1H), 4.43 (dtd, 1H), 4.32 (dtd, 1H), 4.06 (s, 1H), 3.93 (s, 3H), 3.91-3.83 (m, 1H), 3.08 (s, 1H), 2.93 (s, 1H), 2.74-2.55 (m, 3H), 2.37 (dtd, 1H), 2.18-2.01 (m, 3H), 1.98 (s, 3H).

Example 7

1-(2-(1H-Pyrazol-1-yl)ethyl)-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-4-fluoro-1H-benzo[d]imidazole-6-carboxylic acid Isomer 2

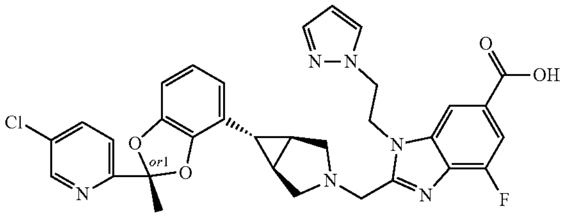

Isomer 2

LiOH monohydrate (7 mg, 0.17 mmol) was added to a solution of methyl 1-(2-(1H-pyrazol-1-yl)ethyl)-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-4-fluoro-1H-benzo[d]imidazole-6-carboxylate Isomer 2 Intermediate 30 (42 mg, 0.067 mmol) in a mixture of THF:$H_2O$ (2:1, 5 mL) and the reaction mixture was stirred at rt for 16 h. The reaction mixture was concentrated in vacuo, and the residue was dissolved in DMSO and purified by preparative HPLC, PrepMethod A, (gradient: 10-50%) to give the lithium salt of the title compound (30 mg, 82%); HRMS (ESI) m/z $[M+H]^+$ calcd for $C_{32}H_{29}ClFN_6O_4$: 615.1918, found: 615.1920; $^1H$ NMR (600 MHz, DMSO-$d_6$) δ 8.68 (d, 1H), 7.95 (dd, 1H), 7.79 (s, 1H), 7.52 (d, 1H), 7.46-7.37 (m, 3H), 6.73-6.64 (m, 2H), 6.46 (d, 1H), 6.12 (s, 1H), 4.68 (t, 2H), 4.51 (t, 2H), 2.96 (dd, 2H), 2.55-2.50 (m, overlapping with solvent peak), 2.16 (s, 1H), 1.95 (s, 3H), 1.88-1.76 (m, 2H).

Example 8a

4-Chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, Isomer 1

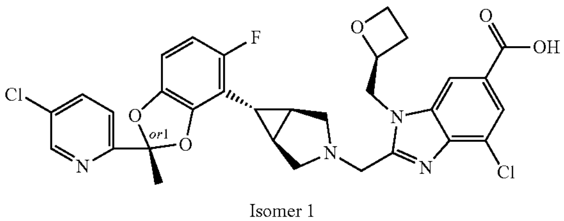 [SMILES: C[C@@]1(c2ccc(Cl)cn2)Oc2ccc(F)c([C@H]3[C@@H]4CN(Cc5nc6c(F)cc(C(=O)O)cc6n5C[C@@H]5CCO5)C[C@@H]43)c2O1]

Isomer 1

LiOH monohydrate (23 mg, 0.54 mmol) was added to a solution of methyl 4-chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Isomer 1 Intermediate 32 (138 mg, 0.22 mmol) in a mixture of THF:$H_2O$ (2:1:15 mL), and the reaction mixture was stirred at rt for 16 h. The reaction mixture was acidified with to pH 3 with 1 M citric acid (aq), diluted with water and extracted with EtOAc. The organic layer was dried over $Na_2SO_4$, filtered and concentrated in vacuo. The residue was purified by preparative HPLC, PrepMethod A, (gradient: 0-50%) to give the title compound Isomer 1 (98 mg, 85%) as a white solid; HRMS (ESI) m/z $[M+H]^+$ calcd for $C_{31}H_{28}Cl_2FN_4O_5$: 625.1416, found: 625.1442; $^1H$ NMR (600 MHz, DMSO-$d_6$) δ 12.92 (s, 1H), 8.70 (d, 1H), 8.31-8.21 (m, 1H), 8.00 (dd, 1H), 7.77 (s, 1H), 7.59 (d, 1H), 6.70 (dd, 1H), 6.60 (dd, 1H), 5.05-4.96 (m, 1H), 4.74 (dd, 1H), 4.58 (dd, 1H), 4.43 (td, 1H), 4.34 (dt, 1H), 4.12 (d, 1H), 3.92 (d, 1H), 3.10 (d, 1H), 2.93 (d, 1H), 2.75-2.54 (m, 3H), 2.42-2.31 (m, 1H), 2.17-2.04 (m, 3H), 1.98 (s, 3H).

Example 8b

4-Chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, Isomer 2

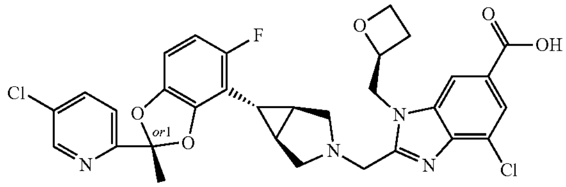

Isomer 2

LiOH monohydrate (25 mg, 0.58 mmol) was added to a solution of methyl 4-chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylate Isomer 2 Intermediate 33 (150 mg, 0.23 mmol) in a mixture of THF:$H_2O$ (2:1:15 mL), and the reaction mixture was stirred at rt for 16 h. The reaction mixture was acidified with to pH 3 with 1 M citric acid (aq), diluted with water and extracted with EtOAc. The organic layer was dried over $Na_2SO_4$, filtered and concentrated in vacuo. The residue was purified by preparative HPLC, PrepMethod A, (gradient: 0-50%) to give the title compound Isomer 1 (111 mg, 90%) as a white solid; HRMS (ESI) m/z $[M+H]^+$ calcd for $C_{31}H_{28}Cl_2FN_4O_5$: 625.1416, found: 625.1454; $^1H$ NMR (600 MHz, DMSO-$d_6$) δ 13.01 (s, 1H), 8.70 (d, 1H), 8.26 (s, 1H), 7.99 (dd, 1H), 7.77 (s, 1H), 7.59 (d, 1H), 6.70 (dd, 1H), 6.60 (dd, 1H), 5.02 (qd, 1H), 4.74 (dd, 1H), 4.58 (dd, 1H), 4.45 (td, 1H), 4.34 (dt, 1H), 4.11 (s, 1H), 3.93 (s, 1H), 3.10 (s, 1H), 2.93 (s, 1H), 2.75-2.58 (m, 3H), 2.41-2.33 (m, 1H), 2.14 (s, 2H), 2.06 (s, 1H), 1.98 (s, 3H).

Example 9

2-(((1R,5S,6R)-6-((R*)-2-(5-Chloropyridin-2-yl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid Isomer 2

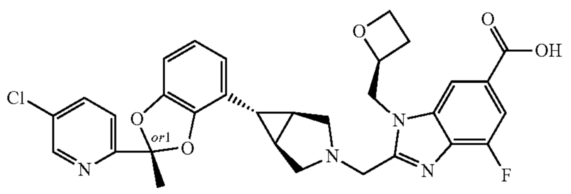

Isomer 2

LiOH monohydrate (19 mg, 0.45 mmol) was added to a solution of methyl 2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 2 Intermediate 38 (108 mg, 0.18 mmol) in a mixture of THF:$H_2O$ (2:1, 5 mL), and the reaction mixture was stirred at rt for 16 h. The reaction mixture was acidified to pH 3 with 10% $NaH_2PO_4$ (aq). The formed precipitate was filtered off and dried in vacuo to give the title compound Isomer 2 (86 mg, 82%) as a white solid; HRMS (ESI) m/z $[M+H]^+$ calcd for $C_{31}H_{29}ClFN_4O_5$: 591.1804, found: 591.1822; $^1H$ NMR (500 MHz, DMSO-$d_6$) δ 12.51 (br s, 1H), 8.69 (d, 1H), 8.15 (s, 1H), 7.99 (dd, 1H), 7.58 (d, 1H), 7.48 (d, 1H), 6.77-6.63 (m, 2H), 6.44 (d, 1H), 5.03 (d, 1H), 4.72 (dd 1H), 4.56 (d, 1H), 4.44 (q, 1H), 4.34 (dd, 1H), 4.10 (d, 1H), 3.89 (d, 1H), 3.10 (d, 1H), 2.95 (d, 1H), 2.74-2.55 (m, 2H), 2.42-2.30 (m, 1H), 2.15 (d, 2H), 1.99 (s, 3H), 1.89-1.77 (m, 2H).

Example 10a 2-(((1R,5S6R)-6-((R*)-2-(5-Chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid Isomer 1

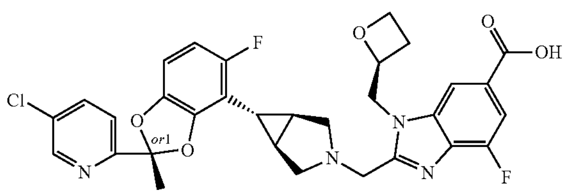

Isomer 1

LiOH monohydrate (13 mg, 0.32 mmol) was added to a solution of methyl 2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 1 Intermediate 40 (80 mg, 0.13 mmol) in a mixture of THF:$H_2O$ (2:1, 5 mL), and the reaction mixture was stirred at rt for 16 h. The reaction mixture was acidified to pH 3 with 10% $NaH_2PO_4$ (aq). The formed precipitate was filtered and dried in vacuo to give the title compound Isomer 1 (65 mg, 85%) as a brown solid; HRMS (ESI) m/z $[M+H]^+$ calcd for $C_{31}H_{28}ClF_2N_4O_5$: 609.1710, found: 609.1756; $^1H$ NMR (400 MHz, DMSO-$d_6$) δ 12.7 (br s, 1H), 8.71 (d, 1H), 8.15 (s, 1H), 8.00 (dd, 1H), 7.59 (d, 1H), 7.49 (d, 1H), 6.71 (dd, 1H), 6.61 (dd, 1H), 5.03 (d, 2H), 4.74 (dd, 1H), 4.58 (d, 1H), 4.52-4.41 (m, 1H), 4.35 (d, 1H), 4.10 (d, 1H), 3.91 (d, 1H), 3.10 (d, 1H), 2.93 (d, 1H), 2.73-2.54 (m, 1H), 2.40 (d, 1H), 2.20-2.01 (m, 4H), 1.99 (s, 3H).

Example 10b 2-(((1R,5S,6R)-6-((R*)-2-(5-Chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid Isomer 2

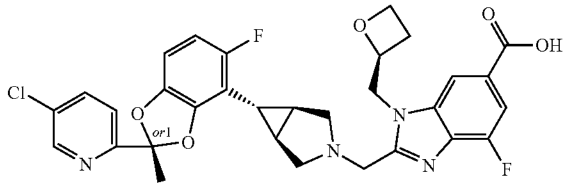

Isomer 2

LiOH monohydrate (14 mg, 0.33 mmol) was added to a solution of methyl 2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 2 Intermediate 41 (84 mg, 0.13 mmol) in a mixture of THF:$H_2O$ (2:1, 5 mL), and the reaction mixture was stirred at rt for 16 h. The reaction mixture was acidified to pH 3 with 10% $NaH_2PO_4$ (aq). The formed precipitate was filtered and dried in vacuo to give the title compound Isomer 1 (59 mg, 82%) as a brown solid; HRMS (ESI) m/z $[M+H]^+$ calcd for $C_{31}H_{28}ClF_2N_4O_5$: 609.1710, found: 609.1754; $^1H$ NMR (400 MHz, DMSO-$d_6$) δ 12.75 (br s, 1H), 8.72 (s, 1H), 8.15 (s, 1H), 8.02 (s, 1H), 7.60 (d, 1H), 7.49 (d, 1H), 6.71 (s, 1H), 6.62 (d, 2H), 5.02 (s, 1H), 4.73 (s, 1H), 4.58 (d, 1H), 4.40 (d, 2H), 4.11 (d, 1H), 3.89 (d, 1H), 3.10 (d, 1H), 2.93 (d, 1H), 2.64 (s, 2H), 2.11 (d, 4H), 1.99 (d, 3H).

Example 11

2-((1R,5S,6R)-6-((R*)-2-(4-Cyano-2-fluorophenyl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid Isomer 2

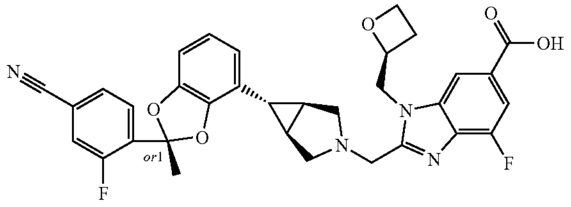

Isomer 2

LiOH hydrate (17 mg, 0.42 mmol) was added to a solution of methyl 2-(((1R,5S,6R)-6-((R*)-2-(4-cyano-2-fluorophenyl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylate Isomer 2 Intermediate 52 (102 mg, 0.17 mmol) in a mixture of THF:$H_2O$ (2:1, 5 mL) and the reaction mixture was stirred at rt for 16 h. The reaction mixture was concentrated at reduced pressure, and the residue was dissolved in DMSO (5 mL) and purified by preparative HPLC, PrepMethod A (gradient: 20-50%), to give the lithium salt of the title compound (8 mg, 8%) as a white solid; HRMS (ESI) m/z $[M+H]^+$ calcd for $C_{33}H_{29}F_2N_4O_5$: 599.2100, found: 599.2100; $^1H$ NMR (400 MHz, DMSO-$d_6$) δ 7.96 (s, 1H), 7.64 (t, 2H), 7.58-7.40 (m, 2H), 6.70 (q, 2H), 6.44 (dd, 1H), 5.07 (d, 1H), 4.68 (dd, 1H), 4.51 (d, 1H), 4.47-4.31 (m, 2H), 4.08 (d, 1H), 3.88 (d, 1H), 3.13 (d, 1H), 2.93 (d, 1H), 2.75 (q, 1H), 2.65 (d, 1H), 2.58-2.51 (m, partly overlapping with solvent), 2.35-2.53 (m, partly overlapping with solvent), 2.21 (d, 1H), 2.02 (s, 3H), 1.84 (t, 2H).

Example 12

4-Chloro-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-1H-benzo[d]imidazole-6-carboxylic acid Isomer 1

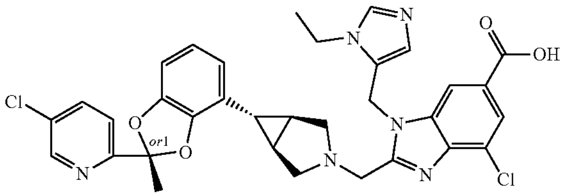

Isomer 1

LiOH hydrate (3.6 mg, 0.087 mmol) was added to a solution of methyl 4-chloro-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-1H-benzo[d]imidazole-6-carboxylate Isomer 1 Intermediate 54 (23 mg, 0.035 mmol) in a mixture of THF:$H_2O$ (2:1, 3 mL) and the reaction mixture was stirred at rt for 16 h. The mixture was concentrated in vacuo, and the residue was dissolved in DMSO (5 mL) and purified by preparative HPLC, PrepMethod A (gradient: 10-50%), to give the lithium salt of the title compound (11 mg, 51%); HRMS (ESI) m/z $[M+H]^+$ calcd for $C_{33}H_{31}Cl_2N_6O_4$: 645.1778, found: 645.1772; $^1H$ NMR (600 MHz, DMSO-$d_6$) δ 8.73 (d, 1H), 8.00 (dd, 1H), 7.84 (s, 1H), 7.76 (s, 1H), 7.59 (t, 2H), 6.78-6.62 (m, 2H), 6.41 (d, 1H), 6.29 (s, 1H), 5.58 (s, 2H), 3.99 (q, 2H), 3.90 (s, 2H), 2.94 (t, 2H), 2.52 (m, partly overlapping with solvent), 2.00 (s, 3H), 1.84-1.73 (m, 3H), 1.15 (t, 3H).

Example 13

2-((1R,5S,6s)-6-(R*)-2-(5-Chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-methoxy-1H-benzo[d]imidazole-6-carboxylic acid Isomer 1

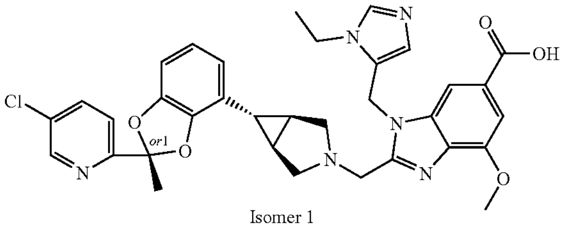 [SMILES: CCn1cncc1Cn1c(CN2C[C@@H]3[C@H](C2)[C@H]3c2cccc3c2O[C@](C)(c2ccc(Cl)cn2)O3)nc2c(OC)cc(C(=O)O)cc21]

Isomer 1

LiOH hydrate (11 mg, 0.26 mmol) was added to a solution of methyl 2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-methoxy-1H-benzo[d]imidazole-6-carboxylate Isomer 1 Intermediate 56 (69 mg, 0.11 mmol) in a mixture of THF:$H_2O$ (2:1, 5 mL) and the reaction mixture was stirred at rt for 16 h. The mixture was concentrated in vacuo, and the residue was dissolved in DMSO (5 mL) and purified by preparative HPLC, PrepMethod A (gradient: 40-90%), to give the lithium salt of the title compound (54 mg, 51%); HRMS (ESI) m/z $[M+H]^+$ calcd for $C_{34}H_{34}ClN_6O_5$: 641.2274, found: 641.2258; $^1H$ NMR (600 MHz, DMSO-$d_6$) δ 8.72 (d, 1H), 8.00 (dd, 1H), 7.63-7.55 (m, 2H), 7.52 (s, 1H), 7.30 (s, 1H), 6.75-6.64 (m, 2H), 6.47-6.36 (m, 1H), 6.29 (s, 1H), 5.50 (s, 2H), 3.97 (q, 2H), 3.88 (s, 3H), 3.82 (s, 2H), 2.91 (dd, 2H), 2.54-2.50 (m, overlapped with solvent), 2.00 (s, 3H), 1.86-1.71 (m, 3H), 1.14 (t, 3H).

Example 14

2-((1R,5S,6s)-6-(R*)-2-(5-Chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylic acid Isomer 1

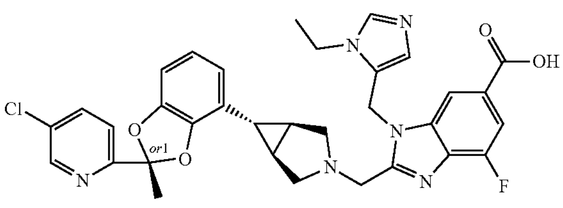

Isomer 1

LiOH hydrate (8 mg, 0.20 mmol) was added to a solution of methyl 2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate Isomer 1 Intermediate 58 (51 mg, 0.079 mmol) in mixture of THF:$H_2O$ (2:1, 5 mL) and the reaction mixture was stirred at rt for 16 h. The reaction mixture was acidified to pH 3 with 1 M citric acid solution (aq), diluted with water and extracted with EtOAc. The organic layer was dried over $Na_2SO_4$, filtered, and concentrated in vacuo. The residue was purified by preparative HPLC, PrepMethod A (gradient: 0-50%), to give the title compound Isomer 1 as a white solid (40 mg, 81%); HRMS (ESI) m/z $[M+H]^+$ calcd for $C_{33}H_{31}ClFN_6O_4$, 629.2074, found: 629.2100; $^1H$ NMR (600 MHz, DMSO-$d_6$) δ 8.73 (d, 1H), 8.00 (dd, 1H), 7.91 (s, 1H), 7.65 (s, 1H), 7.59 (d, 1H), 7.50 (d, 1H), 6.75-6.62 (m, 2H), 6.46-6.34 (m, 2H), 5.68 (s, 2H), 4.03-3.88 (m, 4H), 2.96 (dd, 2H), 2.58-2.50 (m, partly overlapping with solvent), 2.00 (s, 3H), 1.80 (tdd, 3H), 1.12 (t, 3H).

Example 15

2-((1R,5S,6s)-6-((R*)-2-(4-Chloro-2-fluorophenyl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylic acid Isomer 2

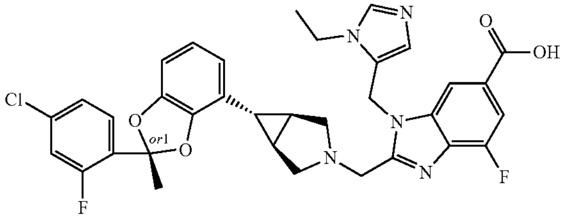

Isomer 2

LiOH hydrate (2.4 mg, 0.057 mmol) was added to a solution of methyl 2-(((1R,5S,6s)-6-((R*)-2-(4-chloro-2-fluorophenyl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylate Isomer 2 Intermediate 60 (15 mg, 0.023 mmol) in a mixture of THF:$H_2O$ (2:1, 3 mL) and the reaction mixture was stirred at rt for 16 h. The reaction mixture was concentrated in vacuo, and the residue was dissolved in DMSO (5 mL) and purified by preparative HPLC, PrepMethod A (gradient 10-50%), to give the lithium salt of the title compound Isomer 2 (7.1 mg, 55%); HRMS (ESI) m/z $[M+H]^+$ calcd for $C_{34}H_{31}ClF_2N_5O_4$: 646.2026, found: 646.2030; $^1H$ NMR (600 MHz, DMSO-$d_6$) δ 7.73 (s, 1H), 7.62 (s, 1H), 7.59-7.49 (m, 2H), 7.44 (d, 1H), 7.33 (dd, 1H), 6.74-6.65 (m, 2H), 6.43 (dd, 1H), 6.34 (s, 1H), 5.58 (s, 2H), 4.00 (q, 2H), 3.89 (s, 2H), 2.97 (d, 2H), 2.56-2.51 (m, overlapping with solvent), 2.01 (s, 3H), 1.86 (s, 3H), 1.15 (t, 3H).

Pharmacological Activity

CHOK1 GLP-1R cAMP Assay

A cell line stably expressing the human GLP-1R receptor (NM_002062.5, including the naturally-occurring variant Leu260Phe) in a CHO-K1 (ATCC® CCL-61™) was used for assay.

GLP-1 receptor mediated agonist activity was determined in a cell-based assay measuring cyclic adenosine monophosphate (cAMP) levels in cells using Homogeneous Time-Resolved Fluorescence (HTRF) cAMP detection kit (CisBio catalog #62AM4PEC, cAMP Gs Dynamic range kit). The cAMP detection method is based on a competitive immunoassay, in which cAMP produced by the cells and cAMP labeled with the dye d2 compete for binding to a Europium- Cryptate-labeled anti-cAMP antibody. The specific HTRF signal is inversely proportional to the concentration of cAMP.

Compounds were added to individual well in 384 well-assay plates (Greiner #784076) using an Echo (LabCyte) dispenser from 10 mM stocks. Varying concentration of compounds were added to wells, and DMSO was used to normalize each well to a volume of 100 nL. A dose response curve of GLP-1(7-36)NH2 (Bachem H-6795) was included in each run. 5 μL of cAMP concentration response standards are applied in specified wells in the assay plates. Cryo-preserved cells are thawed and resuspended in assay buffer pre-heated to 37° C. (20 mM HEPES pH 7.4, 1× Hank's Balanced Salt Solution (HBSS, Life Technologies #14065) supplemented with 0.1% (w/v) bovine serum albumin (Sigma, A-7030). Cells were centrifuged at 250*g for 5 min at rt, and resuspended in room tempered assay buffer to a final density of $0.16*10^6$ cell/mL, to deliver 800 cells/well. 5 μL of assay buffer with 1 mM 3-isobutyl-1-methylxanthin (IBMX; Sigma cat I-7018) was dispensed per well in assay plates using a multidrop combi (Thermo Scientific) subsequently 5 μL of cell suspension was distributed to relevant wells in the assay using a multidrop dispenser. Assay plates were incubated 20 min at rt.

Detection reagents, Europium-Cryptate-labeled anti-cAMP antibody and cAMP labeled with the dye d2, are diluted in lysis buffer, provided by the manufacturer. 5 μL of each detection reagent is supplemented to each assay well using a multidrop dispenser. Assay plates are incubated in the dark for at least one h. The HTRF signal is measured using the HTRF module (excitation: 337 nm, emission A: 665 nm and emission B: 620 nm) in Pherastar FSX (BMG Labtech).

Raw data were converted to pM cAMP using the cAMP standard curve included in each run. Converted data were further analyzed in Genedata Screener (Genedata) and EC50 determinations were made from agonist dose-response curves analyzed with a curve fitting program using a 4-parameter logistic dose response equation (Equation y=A+((B−A)/1+((C/x)^D))) where A is no stimulation, B is full stimulation, C is the EC50 and D is the Hill slope). The percent effect was determined relative to a saturating concentration of a full GLP-1R agonist (GLP-1(7-36)NH2 has 100% effect in this assay setup).

The GLP-1R $EC_{50}$ values for the Example compounds are set forth in Table 1 herein below.

TABLE 1

| Ex. No. | GLP-1R EC50 (nM) |
|---|---|
| 1 | 180 |
| 2 | 14 |
| 3 | 260 |
| 4a | 280 |
| 4b | 61 |
| 5 | 24 |
| 6 | 31 |
| 7 | 260 |
| 8a | 150 |
| 8b | 8.2 |
| 9 | 40 |
| 10a | 19 |
| 10b | 680 |
| 11 | 61 |
| 12 | 30 |
| 13 | 8.1 |
| 14 | 26 |
| 15 | 8.6 |

EndoC cAMP Accumulation Assay

A HTRF cAMP assay (cAMP Gs dynamic kit; CisoBio Cat #62AM4PEJ) was used to identify agonists of GLP-1R in a pancreatic insulinoma cell line (EndoC-βH1). The EndoC-βH1 cell line was sourced from Univercell Biosolutions and is a genetically engineered human pancreatic β cell line which exhibits glucose-inducible insulin secretion. EndoC-βH1cells have detectable GLP-1R messenger ribonucleic acid (mRNA) as detected by quantitative polymerase chain reaction (qPCR). The functionality of GLP-1R signalling in EndoC-βH1 has been demonstrated by Exendin-4 treatment leading to augmented insulin secretion; an effect which is blunted with short hairpin ribonucleic acid (shRNA)-mediated knockdown of GLP-1R. The EndoC-βH1 cell line is a valid model of human beta cells and applicable for screenings to identify novel drug target candidates (*Mol. Metab.,* 2018, 8, 144-157). CisBio HTRF cAMP kits are based on a competitive immunoassay using cryptate-labelled anti-cAMP antibody and d2-labeled cAMP. The detection kit is intended for the direct quantitative determination of cAMP. The specific signal (i.e. energy transfer) is inversely proportional to the concentration of cAMP in the standard or sample. Test compounds (10 mM in DMSO) were diluted into assay buffer (HBSS (Sigma #H8264) supplemented with 25 mM HEPES (Gibco #15630, pH 7.4), 0.1% BSA (Sigma #A3059) and 0.5 mM IBMX (Sigma #I7018) included fresh on the day of the assay) into 96 well U-bottom plates (Greiner #650201). Diluted compounds were transferred to ECHO source polypropylene plates (Labcyte #P-05525) and dose response curves were dispensed acoustically using ECHO 550 into black shallow-well u-bottom 384-well HTRF Assay Plates (Corning 4514).

Cryovials of EndoC-H1 (supplied at $1\times10e^7$ cells/vial) were used directly for screening. The cryovials and were removed from $N_2$(l) and thawed rapidly in a 37° C. water bath. The cells were resuspended in assay buffer and centrifuged at 300 g for 5 min. Cells were resuspended in assay buffer at the appropriate concentration, typically at 12e5 cells per mL (3000 cells per well, dependent on cell batch) and 2.5 μL diluted cells were added to all wells of destination plate by Multidrop combi reagent dispenser (Thermofisher). The plates were incubated at rt for 30 min. The assay was stopped by adding 2.5 μL anti-cAMP cryptate solution to all wells and 2.5 μL cAMP-d2 solution (both diluted 1:20 in lysis buffer) to columns 1-22 by Combi drop. A volume of 2.5 μL cAMP-d2 solution was added to wells E23 to P24 and 2.5 μL lysis buffer added to wells A23 to D24 by multichannel pipette. The plates were incubated at rt for 1 h and read on an Envision plate reader using excitation wavelength of 320 mn and emission of 590 nm and 660 nm.

Raw data from Envision is converted to % DeltaF according to the manufacturer's instructions. Dose response curves are analysed via 4-Parameter Logistical Analysis and assay plate Z' values obtained. Samples are graphed as percentage (%) activation plots compared to GIP (1-42, Bachem H-5645) with assay window defined by negative control as basal cell cAMP levels and positive control are defined by maximum GIP (82.5 nM) signal. GLP-1 (7-36 amide, Bachem H-6795) dose response curve was included on all plates.

The EndoC $EC_{50}$ values for the Example compounds are set forth in Table 2 herein below.

TABLE 2

| Ex. No. | EndoC EC50 (nM) |
|---|---|
| 1 | 69 |
| 2 | 15 |
| 3 | 170 |
| 4a | 350 |
| 4b | 14 |
| 5 | 16 |
| 6 | 19 |
| 7 | 150 |
| 8a | 280 |
| 8b | 9.6 |
| 9 | 58 |
| 10a | 13 |
| 10b | 1900 |
| 11 | 57 |
| 12 | 7.5 |
| 13 | 4.1 |
| 14 | 5.9 |
| 15 | 3 |

Inhibition of phosphodiesterase-3 (PDE3) has been shown to result in an increase in cardiovascular mortality in clinical trials (Movsesian M. A., Kukreja R. C. (2011) Phosphodiesterase Inhibition in Heart Failure. In: Francis S., Conti M., Houslay M. (eds) Phosphodiesterases as Drug Targets. Handbook of Experimental Pharmacology, vol 204. Springer, Berlin, Heidelberg. https://doi.org/10.1007/978-3-642-17969-3_10). Chronic treatment with PDE3 inhibitors has been shown to result in increased mortality, primarily as a result of arrhythmias and sudden death (*Expert Opinion on Investigational Drugs,* 2002, 11, 1529-1536*; J. of Cardiovasc. Trans. Res.,* 2010, 3, 507-515) and it may therefore be an advantage to as far as possible avoid PDE3 inhibitory activity.

PDE3 Assay

Evaluation of the effects of compounds on the activity of the human phosphodiesterase-3A is quantified by measuring the formation of 5'AMP from cAMP using a human recombinant enzyme expressed in a clonal isolate of *Spodoptera frugiperda* cells (Sf9) cells.

The test compound, reference compound or water (control) are added to a buffer containing 40 mM tris(hydroxymethyl)aminomethane (Tris)/HCl (pH 7.4) and 8 mM $MgCl_2$, 450 nMcAMP and 0.25 μCi [$^3$H]cAMP.

Thereafter, the reaction is initiated by addition of the enzyme (about 1 U) and the mixture is incubated for 20 min at 22° C.

For basal control measurements, the enzyme is omitted from the reaction mixture.

Following incubation SPA beads are added. After 30 min at 22° C. under shaking, the amount of [$^3$H]5'AMP is quantified with a scintillation counter (Topcount, Packard).

The results are expressed as a percent inhibition of the control enzyme activity. The standard inhibitory reference compound is milrinone (CAS number 78415-72-2), which is tested in each experiment at several concentrations to obtain an inhibition curve from which its $IC_{50}$ value is calculated.

The PDE3 $IC_{50}$ values for Example compounds and reference compounds are set forth in Table 3 herein below.

TABLE 3

| Ex. No. | PDE3 IC50 (μM) |
|---|---|
| 2 | >10 |
| 10a | >100 |
| Ref Comp A* | 4 |
| Ref Comp B** | 11 |
| Ref Comp C*** | 2 |
| Ref Comp D**** | 5 |

*Ref Comp A may be prepared as disclosed in WO2020103815, Ex 19

**Ref Comp B may be prepared as disclosed in WO2018109607, Ex 4A-01

***Ref Comp C may be prepared as disclosed in WO2021112538, Ex 73 or as disclosed in WO2021081207, Ex 67, or as disclosed in WO2020263695, Ex 3.

***Ref Comp D may be prepared as disclosed in WO2020263695, Ex 2

The invention claimed is:

1. A compound of Formula (I)

(I)

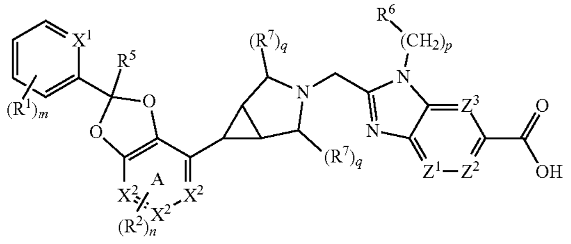

wherein $X^1$ is N or C;

$X^2$ is independently N or C, provided that no more than two atoms in the aromatic ring A are N;

$Z^1$ is N or $CR^3$;

$Z^2$ and $Z^3$ are each independently N or $CR^4$, provided that when $Z^1$ or $Z^3$ is N, $Z^2$ is $CR^4$;

$R^1$ is 0, 1, 2 or 3 substituents independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl and CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from H, $CH_3$, $CFH_2$, $CF_2H$ and $CF_3$;

$R^6$ is selected from (4- to 6-membered)heterocycloalkyl, (5- to 6-membered)heteroaryl, CN, $C_{1-4}$alkyl, O($C_{1-4}$ alkyl), S($C_{1-4}$alkyl), cyclopropyl, cyclobutyl, O(cyclopropyl) or S(cyclopropyl), wherein said (4- to 6-membered)heterocycloalkyl and (5- to 6-membered)heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

$R^7$ is independently selected from F, $C_{1-2}$alkyl and $OC_{1-2}$alkyl, wherein said $C_{1-2}$alkyl is substituted by 0, 1, 2 or 3 F;

m is 1, 2 or 3;

n is 0 or 1;

p is 1, 2 or 3; and q is 0, 1 or 2;

or a pharmaceutically acceptable salt thereof.

2. The compound according to claim 1 of Formula (Ia)

(Ia)

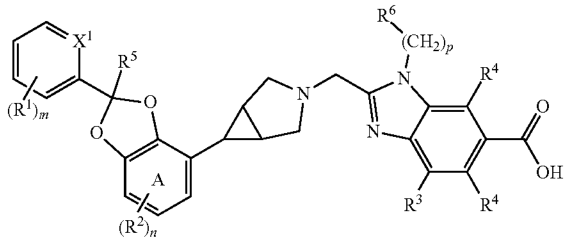

wherein $X^1$ is N or C;

$R^1$ is independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl and CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from H, $CH_3$, $CFH_2$, $CF_2H$ and $CF_3$;

$R^6$ is selected from (4- to 6-membered) heterocycloalkyl, (5- to 6-membered) heteroaryl, CN, $C_{1-4}$alkyl, O($C_{1-4}$ alkyl), S($C_{1-4}$alkyl), cyclopropyl, cyclobutyl, O(cyclopropyl) or S(cyclopropyl), wherein said (4- to 6-membered) heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

m is 0, 1, 2 or 3;

n is 0 or 1; and p is 1, 2 or 3;

or a pharmaceutically acceptable salt thereof.

3. The compound according to claim 2, wherein $X^1$ is N;

$R^1$ is independently selected from F, Cl and CN;

$R^2$ is selected from F, Cl and CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$ and $OCH_3$;

$R^5$ is selected from H, $CH_3$, $CFH_2$, $CF_2H$ and $CF_3$;

$R^6$ is selected from (4- to 6-membered) heterocycloalkyl and (5- to 6-membered) heteroaryl wherein said (4- to 6-membered) heterocycloalkyl and (5- to 6-membered) heteroaryl is substituted by 0 or 1 $C_{1-2}$alkyl;

m is 0, 1 or 2;

n is 0 or 1; and p is 1;

or a pharmaceutically acceptable salt thereof.

4. The compound according to claim 1 selected from:

2-(((1R,5S,6R)-6-(2-(4-Chloro-2-fluorophenyl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-((R*)-2-(4-chloro-2-fluorophenyl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, 2-(((1R,5S,6R)-6-(2-(5-Chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-((R*)-2-(5-Chloropyridin-2-yl)-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, 4-Chloro-2-(((1R,5S,6R)-6-((R*)-2-(5-chloropyridin-2-yl)-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-(2-(5-Chloropyridin-2-yl)-5-fluoro-2-methylbenzo[d][1,3]dioxol-4-yl)-3-azabicyclo[3.1.0]hexan-3-yl)methyl)-4-methoxy-1-(((S)-oxetan-2-yl)methyl)-1H-benzo[d]imidazole-6-carboxylic acid, 1-(2-(1H-Pyrazol-1-yl)ethyl)-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-4-fluoro-1H-benzo[d]imidazole-6-carboxylic acid, 4-Chloro-2-(((1R,5S,6R)-6-((R*)-2-(5-chloropyridin-2-yl)-5-fluoro-2-methylbenzo[d][1,3]dioxol-4-yl)-3-azabicyclo[3.1.0]hexan-3-yl)methyl)-1-(((S)-oxetan-2-yl)methyl)-1H-benzo[d]imidazole-6-carboxylic acid, 2-(((1R,5S,6R)-6-((R*)-2-(5-Chloropyridin-2-yl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid, 2-(((1R,5S,6R)-6-((R*)-2-(5-Chloropyridin-2-yl)-5-fluoro-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid, 2-(((1R,5S,6R)-6-((R*)-2-(4-Cyano-2-fluorophenyl)-2-methylbenzo[d][1,3]dioxol-4-yl)-3-azabicyclo[3.1.0]hexan-3-yl)methyl)-4-fluoro-1-(((S)-oxetan-2-yl)methyl)-1H-benzo[d]imidazole-6-carboxylic acid, 4-Chloro-2-(((1R,5S,6s)-6-((R*)-2-(5-chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-1H-benzo[d]imidazole-6-carboxylic acid, 2-(((1R,5S,6s)-6-((R*)-2-(5-Chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-methoxy-1H-benzo[d]imidazole-6-carboxylic acid, 2-(((1R,5S,6s)-6-((R*)-2-(5-Chloropyridin-2-yl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylic acid, and 2-(((1R,5S,6s)-6-((R*)-2-(4-Chloro-2-fluorophenyl)-2-methylbenzo[d][1,3]dioxol-4-yl)-3-azabicyclo[3.1.0]hexan-3-yl)methyl)-1-((1-ethyl-1H-imidazol-5-yl)methyl)-4-fluoro-1H-benzo[d]imidazole-6-carboxylic acid, or a pharmaceutically acceptable salt thereof.

5. A pharmaceutical composition comprising a compound according to claim 1, or a pharmaceutically acceptable salt thereof, in admixture with a pharmaceutically acceptable adjuvant, diluents or carrier.

6. A method of treating, or reducing the risk of, cardiovascular disease or metabolic conditions which comprises administering to a person suffering from or at risk of, said disease or condition, a therapeutically effective amount of a compound according to claim 1, or a pharmaceutically acceptable salt thereof.

7. The method according to claim 6, wherein said disease is type 2 diabetes.

* * * * *